United States Patent [19]

Raziuddin et al.

[11] Patent Number: 5,518,885

[45] Date of Patent: May 21, 1996

[54] ERBB2 PROMOTER BINDING PROTEIN IN NEOPLASTIC DISEASE

[75] Inventors: Raziuddin, Frederick, Md.; Fazlul H. Sarkar, Rochester Hills, Mich.

[73] Assignees: The United States of America as represented by the Department of Health & Human Services, Washington, D.C.; Wayne State University, Detroit, Mich.

[21] Appl. No.: 229,515

[22] Filed: Apr. 19, 1994

[51] Int. Cl.$^6$ .............................. C12Q 1/68; G01N 33/53
[52] U.S. Cl. .................................................. 435/6; 435/7.1
[58] Field of Search .......................................... 435/7.1, 6

[56] References Cited

U.S. PATENT DOCUMENTS

| | | | |
|---|---|---|---|
| 4,935,341 | 6/1990 | Bargmann et al. | 435/6 |
| 4,968,603 | 11/1990 | Slamon et al. | 435/6 |
| 5,183,884 | 2/1993 | Kraus et al. | 536/23.5 |

FOREIGN PATENT DOCUMENTS

| | | |
|---|---|---|
| 0505148A1 | 9/1992 | European Pat. Off. . |
| WO92/20798 | 11/1992 | WIPO . |

OTHER PUBLICATIONS

Sarkar et al. "c–er–B–2 Promoter–specific DNA–binding Protein Isolated from Human Breast Cancer . . . " J. Biol. Chem. 269(16):12285–12289, Apr. 22, 1994.
Wels, W. et al., "Selective Inhibition of Tumor Cell Growth by a Recombinant Single–Chain Antibody–Toxin Specific for the erbB–2 Receptor," Cancer Research, 52:6310–6317 (Nov. 15, 1992).
Yu D. et al., "The Retinoblastoma Gene Product Suppresses neu Oncogene–induced Transformation via Transcriptional Repression of neu," J. Biol. Chem., 267(15):10203–10206 (1992).
Yan D–H et al., "Identification and Characterization of a Novel Enhancer for the Rat neu Promoter," Mol. Cell. Biol., 11(4):1875–1882 (Apr. 1991).
Yan D–H. et al., "Repressed Expression of the HER–2/c–erbB–2 Proto–Oncogene by the Adenovirus E1a Gene Products," Oncogene, 6:343–345 (1991).
Gusterson B. A. et al., "c–erbB–2 Expression in Benign and Malignant Breast Disease," Br. J. Cancer, 58:453–457 (1988).
Kokai Y. et al., "Stage–and Tissue–Specific Expression of the neu Oncogene in Rat Development," Proc. Natl. Acad. Sci. USA, 84:8498–8501 (Dec. 1987).
Hung M. C. et al., "Molecular Cloning of the neu Gene: Absence of Gross Structural Alteration in Oncogenic Alleles," Proc. Natl. Acad. Sci. USA, 83:261–264 (Jan. 1986).
Jones K. A. et al., "Two Distinct Transcription Factors Bind to the HSV Thymidine Kinase Promoter In Vitro," Cell, 42:559–572 (Sep. 1985).
Miyamoto N. G. et al., "Stimulation of In Vitro Transcription by the Upstream Element of the Adenovirus–2 Major Late Promoter Involves a Specific Factor," Nucl. Acids Res., 12(23):8779–8798 (1984).

Primary Examiner—George C. Elliott
Assistant Examiner—Terry A. McKelvey
Attorney, Agent, or Firm—Needle & Rosenberg

[57] ABSTRACT

The present invention provides a purified and isolated DNA-binding protein, HPBF, which specifically binds to the promoter region of the Her-2/neu (ERBB2/c-erbB-2) gene sequence, the presence of which provides an early indication of transition to a cancerous state has been found. The present invention also provides bioassays for screening substances for the ability to inhibit HPBF activity, the ability to inhibit the mitogenic activity of HPBF and the ability to inhibit HPBF production. The present invention further provides methods of inhibiting the biological activity mediated by HPBF comprising preventing the HPBF from binding to the promoter region of the ERBB2 gene sequence.

14 Claims, 2 Drawing Sheets

ERBB2 PROMOTER BINDING PROTEIN IN NEOPLASTIC DISEASE

BACKGROUND OF THE INVENTION

1. Field of the Invention

The present invention relates generally to the field of medical diagnosis and specifically for monitoring the presence of neoplastic diseases at an early stage to allow early therapeutic intervention.

2. Background Art

Currently, early detection of breast cancer in humans, particularly in women, depends on self-examination and mammography. However, routine mammography is not recommended for women under 50. Therefore, breast cancers in younger women tend not to be found until more advanced with a correspondingly poorer prognosis. Screening methods are needed to identify early stages of the transition of normal epithelial cells towards carcinoma in situ before the subsequent development of invasive and metastatic cancer.

Breast cancer appears to be genetically and/or morphologically, a heterogeneous disease and multiple mechanisms are responsible for the ultimate development of breast carcinoma from normal epithelial cells. The Her-2/neu (ERBB2/c-erbB-2) gene sequence (SEQ ID NO:9), hereinafter referred to as ERBB2, appears to be one of the primary genes responsible for the transition of normal epithelial cells towards carcinoma in situ and the subsequent development of invasive and metastatic cancer. However, by the time the gene product of ERBB2 is measurable, prognosis is not good. A means of identifying the initiation step for ERBB2 gene activity and interfering with that step are necessary for greater success in early identification and treatment of breast cancer.

Significant progress has been made at the molecular level to dissect the role of the ERBB2 gene and its association with breast cancer. However, mechanisms that control or initiate the activity of the ERBB2 gene have not been available to give early prediction or treatment of breast cancer. The results of some of these molecular studies are described herein.

Histologically, breast cancer comprises about 70–85% classified as ductal carcinoma; the next largest subgroup is referred to as lobular carcinoma. These two major classes of breast cancer comprise more than 80–95% of breast cancer in humans. It has been estimated that 5–15% of breast cancer in women under 50 years of age is associated with a genetic propensity for the disease.[1-13] Several recent studies have elucidated some of the inherited mechanisms which are at work in breast cancer.[14-17] A recent review has described various molecular determinates of growth, angiogenesis and metastases which may play a role in breast cancer.[18] In addition, the ERBB2 gene has recently been documented to be prognostically important in breast cancer.[43,45,56,69]

The ERBB2 gene is the human counterpart of the rat neu oncogene (SEQ ID NO:12), originally identified in ethyl nitroso-urea induced rat neuroglioblastomas by Weinberg and co-workers.[19,20] The ERBB2 oncogene codes for a protein of 185,000 dalton molecular weight (p185 product), and the product is similar in overall organization and primary amino acid sequence to the epidermal growth factor receptor (EGFR).[21-23] A possible ligand for ERBB2 has recently been described.[24-26] The ERBB2 gene is not overexpressed in benign breast tissue,[27] but significantly overexpressed in 60% of carcinoma in situ (preneoplastic lesion of breast carcinoma) and in about 30% of invasive cancer.[28-30]

The p185 product of the ERBB2 gene is a growth factor receptor with intrinsic protein tyrosine kinase activity[31,32] which, when deregulated, or disregulated, results in unrestrained growth and cell transformation.[32-34] The transforming potential of the ERBB2 gene is also related to the levels of protein expression. This proto-oncogene is also frequently amplified in many human tumors and in cell lines derived from tumors.[33,35,38] ERBB2 gene overexpression in the absence of gene amplification has also been described.[33,36,38] The ERBB2 gene product is a potent oncoprotein when overexpressed in NIH-3T3 cells.[34] In a transgenic mouse model experiment, transgenic mice were created[39,40] expressing the activated form of the rat neu proto-oncogene, under the control of steroid inducible promoter, and uniformly developed mammary adenocarcinoma. In addition, ERBB2 gene amplification in human breast tumor is often associated with poor patient prognosis[33,38] The overexpression of ERBB2 has also been associated with poor prognosis in non-small cell lung cancer.[41,85]

A convincing body of clinical and experimental evidence thus supports the role of ERBB2 protein in the progression of human cancers characterized by the overexpression of this oncogene product. Important aspects of this evidence include the poor prognosis of breast, ovarian and non-small cell carcinoma patients whose tumors overexpress ERBB2 protein, as well as observations which indicate that modulation of ERBB2 protein activity by a monoclonal antibody can reverse many of the properties associated with tumor progression mediated by growth factor receptor.[42]

A recent study[43] of 209 consecutive female patients with invasive operable breast cancer from a defined urban population observed for a median of 30 years demonstrated that fifty-five patients (26%) had cancer and a positive ERBB2 oncoprotein stain reaction. They had significantly reduced 10 and 25 years survival rates as compared with those patients who had a negative stain reaction in their cancer (31% versus 48% and 31% versus 39% respectively with a P value=0.004). ERBB2 gene expression was also found to be associated with reduced survival among patients who had axillary nodal metastases (P value=0.003) but not among those patients who did not have metastases. ERBB2 expression was related to the ductal histologic type, poor histologic grade and high mitotic count, but not to tumor size, axillary nodal status, DNA ploidy or S-phase fraction. In a multivariate analysis among patients with nodal metastases, ERBB2 expression was found to be an independent prognostic factor (P value=0.004) that predicted poor survival. Based on these data, it was concluded that ERBB2 oncoprotein expression has long-term prognostic significance for predicting poor survival in breast cancer and it has an independent prognostic value among patients who presented with axillary nodal metastases. The mean survival time for the women with ERBB2 expressing group is only 29 months compared to the mean survival time of 110 months of the women with nonexpressing cancer. The difference between the survival curve is the greatest at approximately five years from the diagnosis (37% versus 64%) and diminished toward the end of the follow-up, which indicates that ERBB2 expressing cancers usually progress rapidly and are fatal. The result that ERBB2 expression predicts poor survival is contradictory to the opinion that it could only be a marker for drug resistance,[44] not a marker for poor prognosis.

Overexpression of the ERBB2 oncogene has previously been correlated with poor prognosis in patients with infiltrating breast carcinoma.[33] The authors reported a 35% difference in survival at four years for node positive patients with ERBB2 positive tumors.[33] This finding was emphasized in later studies with large numbers of patients.[45] It appears that the inconsistencies in the relationship between ERBB2 overexpression and mammary carcinoma are related to its correlation with tumor type. In studies of infiltrating carcinoma, the proportion of tumors showing overexpression has ranged from 10–30%;[28–30,33,46–47] in carcinoma in situ, the incidence of overexpression is much higher, in the order of 60%.[28–30]

Several studies[45,48–50] have clearly shown that there is no loss of ERBB2 expression when invasive tumors progress from a pure in situ carcinoma. Therefore, there must be some other reason why fewer infiltrating tumors overexpress ERBB2. The nuclear sizes of the in situ and infiltrating components were also very similar and as has been found previously for in situ disease, almost all of the ERBB2 positive cases contained some large nuclei. A study[51] has suggested that there are at least three groups of infiltrating tumors:

Group 1—those composed of cells with small nuclei which have arisen from small cell cribriform/micropapillary ductal carcinoma in situ. These have a low rate of proliferation and of ERBB2 overexpression.

Group 2—tumors composed of large cells which have arisen from large cell comedo ductal carcinoma in situ. These have a high rate of proliferation and ERBB2 overexpression.

Group 3—tumors composed of cells with variable nuclear sizes, but including some large nuclei, over half of which have a high rate of proliferation, but none of which overexpress ERBB2.

The hypothesis is that the latter group of tumors only have a transient in situ period and quickly become invasive. Because of this rapid progression to invasion, these tumors were not found in these studies of pure ductal carcinoma in situ. They made only a minor contribution to that study of tumors with a prominent ductal carcinoma in situ component accompanied by a variable infiltrating component but have become very obvious in this particular study. This could explain the dilution of overall ERBB2 positivity seen in studies of infiltrating tumors when compared to pure in situ tumors. If this is so, it could be accepted that the presence of ERBB2 overexpression is a marker of poor prognosis, since the ERBB2 positive in situ tumors are always composed of large cells, usually of comedo pattern and there are data to suggest that such tumors have a greater invasive potential than other patterns of in situ carcinoma.[52–55] In cases of infiltrating carcinoma, the ERBB2 positive tumors again contain large cells and are rapidly proliferating, both factors being associated with a poor prognosis. Whereas tumors with small nuclei and tumors with low proliferative activity are nearly always ERBB2 negative, there are also significant numbers of ERBB2 negative tumors which contain at least some large cells, and many of these tumors have a high rate of proliferation. As already suggested, it is possible that this group of tumors has only a transient in situ stage.

Finally, another recent study[56] demonstrated that tumors from 16% of the node negative patients and 19% of the node positive patients were ERBB2 positive. In both groups, ERBB2 positively correlated with negative progesterone receptor, negative estrogen receptors and high tumor grade. The expression of ERBB2 was prognostically significant for node positive, but not for node negative patients. Tumors with overexpression of ERBB2 oncogene were less responsive to cyclophosphamide methotrexate and fluorouracil containing adjuvant therapy regimens than those with a normal amount of gene product, suggesting worse tumor behavior. For node positive patients, the effect of prolonged duration therapy on disease free survival was greater for patients without ERBB2 overexpression than those with ERBB2 overexpression. Similarly, for node negative patients, the effect of perioperative treatment on disease free survival was greater for those without ERBB2 overexpression than for those with ERBB2 overexpression.

U.S. Pat. Nos. 4,935,341 to Bargmann et al., issued Jun. 19, 1990, 4,968,603 to Slamon et al. issued Nov. 6, 1990 and 5,183,884 to Kraus et al., issued Feb. 2, 1993, provide methods relating to the identification of ERBB2 gene expression, overexpression and prognostic indicators of breast cancer based on the ERBB2 gene product. The Slamon et al. '603 patent discloses amplification of the ERBB2 oncogene and its relationship to the status of breast and ovarian adenocarcinomas. In particular, the degree of gene amplification provides prognostic utility for breast cancer. The Bargmann et al. '341 patent discloses mutations in the ERBB2 gene which result in an oncogene state and provide an oligonucleotide probe capable of hybridizing to the mutated region. The Kraus et al. '884 patent discloses a DNA fragment distinct from EGFR and the ERBB2 gene, designated as ERBB-3. Marked elevation of ERBB-3 mRNA levels were demonstrated in certain human mammary tumor cell lines.

The above research and patents do not provide information that allows screening to identify earlier stages of the transition of normal epithelial cells towards carcinoma in situ before the subsequent development of invasive and metastatic cancer. These results indicate that the ERBB2 gene is extremely important in a significant percentage of breast cancers and the regulation of expression is perhaps a key determining factor in breast cancer development and progression. If the regulation can be controlled, transition to a cancerous state can be stopped.

Recent studies of cloning and characterization of an ERBB2 promoter have compared mouse neu promoter (SEQ ID NO:15) with human ERBB2 promoter.[57] (SEQ ID NO:10; SEQ ID NO:11) The presence of CAAT box and lack of a TATAA motif is one way in which the mouse neu promoter differs from the human ERBB2 promoter[58] but is similar to the rat neu promoter.[59] (SEQ ID NO:13; SEQ ID NO:14) The GGA repeats observed between −204 and −184 (with respect to the translational start "ATG" codon) of the mouse neu promoter are also seen in rat[59] neu and human ERBB2 promoters.[58] A sequence consensus for SP1 is located at −211 of the mouse neu promoter. SP1 consensus sequences are also seen in rat neu promoter and the human ERBB2 promoter in an analogous region. The sequence GCCGCCGC at −140 in the mouse neu promoter is similar to the binding site for G-CSF[60] and is also observed in the rat neu promoter but not in the human ERBB2 promoter. A sequence similar to the OTF 1 motif, [61,62] but differing by one nucleotide (ATGCAAAC instead of ATGCAAAT), is located at position −462. A similar sequence is also seen in the rat neu promoter and human ERBB2 promoters at equivalent positions. Sequences with homology to the AP2 consensus sequence (YSSCCMNSSS[8])(SEQ ID NO:16) are located at −328 and −106 of the mouse neu promoter gene; similar sequences are also found in the corresponding regions of the rat neu promoter and human ERBB2 promoter.

A novel transcription factor termed "RNF"[64] was found to bind to the promoter of the rat neu gene. The binding sequence for this factor is also present in both the mouse (−439) neu promoter and human ERBB2 promoter. The GGTGGGGGGG sequence (SEQ ID NO:17) termed "GTG" enhancer, which is involved in autorepression of the rat neu transcription[59] is located at position −249 to −240 in the mouse neu promoter. However, the corresponding region of the human ERBB2 promoter is different. Conservation of transcription factor sequences among these three species may imply a conserved function. It is not known at the present time whether those sequences that are different between rodent and human genes such as CAAT and TATAA box, GTG enhancer and other motifs might represent species specific functions.

This information, together with the fact that multiple transcriptional initiation sites are mapped in both the rat neu and human ERBB2 genes, makes it likely that the TATAA sequence in the human ERBB2 promoter does not function as a transcriptional TATAA box. The previous studies on rat neu and human ERBB2 promoters focused mainly on a region within 1 Kb upstream from the transcriptional initiation sites. The current studies on the mouse neu promoter[57] have lead to identification of a silencer region approximately three Kb upstream from the transcriptional initiation site, similar sequences have not yet been reported in human ERBB2 promoter. An estrogen responsive region has been found within the rat neu promoter region.[70]

It has been reported that the expression of the ERBB2 gene is tissue specific and developmentally regulated.[65] Transcriptional regulation, therefore, may be one of the mechanisms (factor) leading to overexpression of ERBB2 gene in human cancer cells. Therefore, regardless of the relative distances from the transcriptional initiation site, identification of silencer and enhancer sequences controlling ERBB2 transcription provides important information that may allow clinical information to be obtained for studying transcriptional mechanisms resulting in cancer and understanding the biological role of ERBB2 gene regulation in breast cancer development, heterogeneity, progression and recurrence.

Primary gene induction or repression in eukaryotes does not require de novo protein synthesis, suggesting the involvement of post-translational modifications as well. In a recent review,[67] it was summarized that many different types of stimuli that affect gene expression also led to the activation of protein kinases; it is likely that transcription factor function will be directly regulated by phosphorylation. Even though other types of post-translational modifications will undoubtedly be important in regulating transcription factor function, phosphorylation seems to be one of the most important functions which has been studied recently.[67–68]

In summary, first, a transcription factor can be sequestered in the cytoplasm and rendered inactive through lack of access to the target sequences. Phosphorylation of the factor itself, or a cytoplasmic anchor protein allows translocation of the transcription factor into the nucleus, where it acts, generally by binding to the DNA at a specific site by protein-DNA interaction.[73] Second, the DNA-binding activity of nuclear transcription factor can be modulated by phosphorylation either positively or negatively.[67–68] Third, phosphorylation can affect the interaction of transcription factor transactivation domains with the transcriptional machinery.[67–68] These possibilities are by no means mutually exclusive and in principle phosphorylation at multiple sites by different protein kinases can result in regulation at several distinct levels. Nuclear translocation of various transcription factors modulated by phosphorylation has been demonstrated recently.[72]

It has been shown that in unstimulated cells, with the notable exception of B cells, NF$\chi$B (nuclear factor $\chi$B) is retained in the cytoplasm in an inactive complex with the intermediary protein (L$\chi$B), which cannot bind DNA.[73,74] In response to various stimuli, including the phorbol-ester TPA, the I$\chi$B-NF$\chi$B complex dissociates and NF$\chi$B DNA-binding activity is detected in the nucleus.[73] DNA binding activity can be revealed in unstimulated cytoplasmic extracts by a number of means including treatment with sodium deoxycholate, which dissociates the I$\chi$B-NF$\chi$B complex.[74] Therefore, there is much evidence to suggest that a transcription factor can be found in the cytoplasmic extracts, as well as in the nuclear extract.[67] A phosphorylation-dephosphorylation mechanism for the translocation of transcription factor in numerous systems by protein kinase A and protein kinase C has been demonstrated as indicated earlier.[67–68] Almost every eukaryotic transcription factor that has been analyzed in detail has proved to be phosphorylated. In most cases, however, the functional consequences of such phosphorylations, if any, are largely unknown.

There are only a few possible mechanisms proposed for the regulation of ERBB2 gene expression which are summarized as follows:

(i) A recent report has suggested that the E3 region of adenovirus induces down regulation of epidermal growth factor receptor. A similar repression of ERBB2 expression has also been documented, however, the repressed expression of ERBB2 is not through the E3 region of the adenovirus. The repression of ERBB2 expression is accomplished by E1A gene product, and it specifically repressed ERBB2 gene expression at the RNA level[75] and full basal promoter activity of ERBB2 gene has been shown to be retained by two fragments of the ERBB2 5' region (−759 to−724 and −396 to −24 base pair).

(ii) Functional inactivation of both alleles of the retinoblastoma susceptibility gene (RB) plays an important role in the etiology of both sporadic and familial retinoblastomas and several other types of human cancers, including breast cancer.[76,77] The RB gene may have cell cycle control function.[78,79] RB protein function may vary during the cell cycle because it shows cell cycle dependent changes in phosphorylation and RB protein can be phosphorylated by the cell cycle kinase p34 cdc2[80] RB protein can also complex with the transcription factor E2F and inhibit E2F binding to the promoters of several cellular proliferation related genes.[81] Recent studies revealed that RB protein can negatively regulate the immediate early genes of c-fos and c-myc expression at the transcriptional level in NIH-3T3 cells.[82,83] RB also stimulates the growth inhibitory factor TGF-β1 expression in certain cell types and subsequently suppresses cell growth.[84] Taken together, all of these results suggest that RB may limit the progression of cells through the cell cycle by sequestering a variety of nuclear proteins involved in growth regulatory gene transcription. As indicated earlier the amplification and overexpression of ERBB2 is involved in human breast and lung cancers.[38,85] Interestingly, inactivation of the RB gene has also been implicated in the oncogenesis of human breast and lung cancers[77,86] and may suggest the possible molecular link between RB and the ERBB2 gene in the development and progression of breast cancer. A recent study has shown that the RB protein can bind specifically with a GTG-GGGGGGG sequence (SEQ ID NO:18) in the ERBB2 promoter and suppress the promoter function. This study has concluded that the RB protein suppresses ERBB2 induced transformation by suppressing the ERBB2 promoter activity.[87]

(iii) An interesting feature of the human ERBB2 gene promoter is the presence of two different types of regulatory elements: a CAAT box and SP1 binding sites. Transcription from the three most downstream RNA start sites appears to be controlled by the CAAT box and the TATA box, because these are respectively about 30 bp and 80 bp upstream of the early start sites and these distances are consistent with those in many other eukaryotic promoters.[88] On the other hand, transcription from the fourth RNA start site located further upstream seems to be controlled at least partly by SP1. In contrast with the ERBB2 gene promoter, the promoter region of the human epidermal growth factor receptor (EGFR) gene does not contain either a TATA box or a CAAT box but has 5 SP1 binding sites. Therefore, the expression of the ERBB2 gene may be regulated by the transcription factor SP1, a CAAT box binding protein and a TATA box binding protein,[89-91] whereas the expression of the EGFR gene seems to be regulated by SP1 but not by the latter two proteins.

Since the ERBB2 gene appears to be important in breast cancer, treatment modalities have been reported in the literature employing strategies which target this gene. A recent report[71] used a monoclonal antibody coupled to a toxin to target the extracellular domains of the ERBB2 receptor protein which are overexpressed on human breast and ovarian tumor cells in vitro. However, this is again late in the stage of the transition of normal epithelial cells to cancer. As described earlier, ERBB2 expressing cancers usually progress rapidly and are fatal. Treatment and diagnosis needs to be at an earlier stage, while the cells are still only showing hyperplasia.

SUMMARY OF THE INVENTION

The present invention provides a purified and isolated DNA-binding protein which specifically binds to the promoter region of the c-erbB-2 gene sequence (Her-2/neu promoter binding factor: HPBF).

The present invention also provides antibodies which specifically bind H-PBF. The present invention further provides a bioassay for determining the mount of HPBF in a biological sample comprising contacting the biological sample with a nucleic acid or antibody to which the HPBF binds under conditions such that an HPBF/nucleic acid complex or an HPBF/antibody complex can be formed and determining the amount of the complex, the amount of the complex indicating the mount of HPBF in the sample.

The present invention also provides a method of detecting the presence of a cancer in a subject and determining the prognosis of a subject having cancer comprising determining the presence of a detectable amount of HPBF in a biopsy from the subject, the presence of a detectable amount of HPBF, relative to the absence of HPBF in a normal control indicating the presence of cancer and a decreased chance of long-term survival.

The present invention further provides a DNA isolate encoding HPBF.

In addition, the present invention provides a bioassay for screening substances for ability to inhibit the activity of HPBF comprising administering the substance to a cell construct comprising the promoter region of ERBB2 linked to a reporter gene and an activated gene encoding HPBF and determining the amount of the reporter gene product and selecting those substances which inhibit the expression of the reporter gene product.

The present invention also provides a bioassay for screening substances for the ability to inhabit the mitogenic activity of HPBF in NIH3T3 cells comprising administering the substance to the cells, administering HPBF to the cells, determining the mitogenic activity of HPBF in the substance-treated cells and selecting those substances which inhibit the mitogenic activity of HPBF in the cells.

The present invention further provides a bioassay for screening substances for the ability to the inhibit the production of HPBF comprising administering the substance to a cell having an activated gene encoding HPBF and determining the amount of HPBF produced and selecting those substances which inhibit the production of HPBF.

Finally, the present invention provides a method of inhibiting a biological activity mediated by HPBF comprising preventing the HPBF from binding to the promoter region of the ERBB2 gene sequence wherein the binding to the promoter region is prevented by an antisense nucleotide sequence or wherein the binding to the promoter region is prevented by a nongenomic nucleic acid sequence to which the HPBF binds.

BRIEF DESCRIPTION OF THE DRAWINGS

Other advantages of the present invention will be readily appreciated as the same becomes better understood by reference to the following detailed description when considered in connection with the accompanying drawings wherein.

DESCRIPTION OF THE PREFERRED EMBODIMENTS

Figure 1:
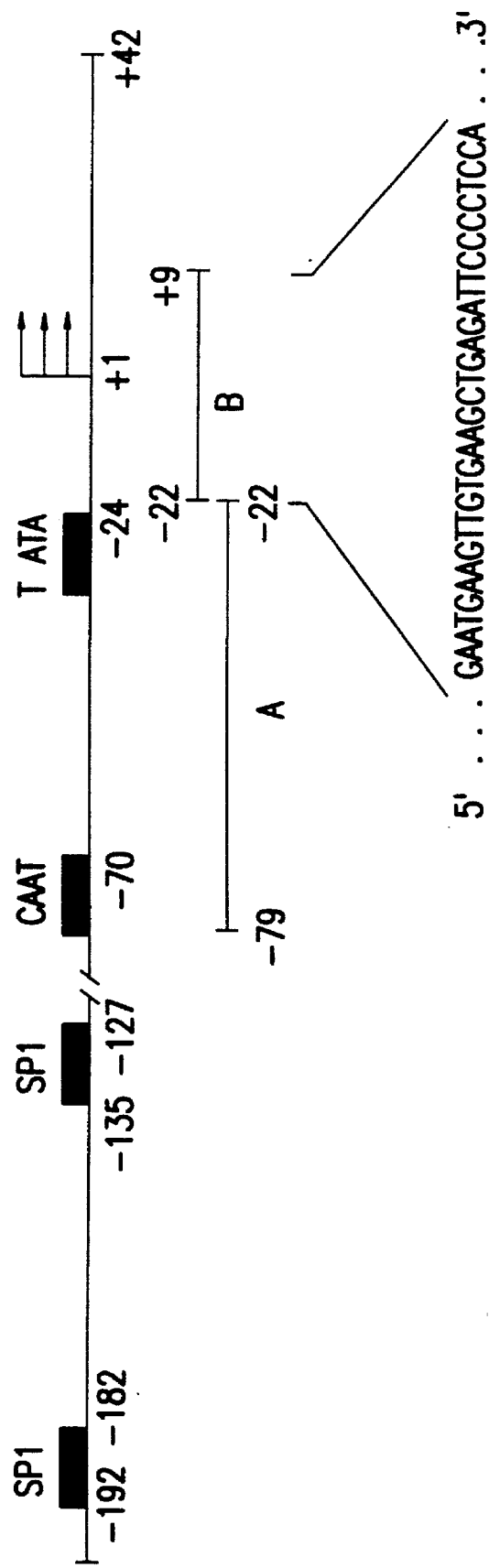
FIG. 1 is a representation of a partial physical map of ERBB2 5' region including the promoter area, where several binding factors are indicated in black boxes. The probe B (SEQ ID NO:19), which is the immediate 5' promoter region, spans −22 to +9 relative to the last transcription start site in the ERBB2 promoter.

The present invention may be understood more readily by reference to the following detailed description of specific embodiments and the Examples and Figures included therein.

As used herein, "a" can mean one or more depending on its context.

According to the present invention, a purified and isolated DNA-binding factor which specifically binds to the promoter region of the ERBB2 gene sequence (Her-2/neu promoter binding factor: HPBF) has been found, as detailed in Examples 1–4 here below. (The factor has also been designated herein as ERBB2 promotor binding protein: EPBP and as Tumor Enhancer Factor: TEF.) The factor was determined to be a protein as detailed in Example 5 below. The protein includes a peptide generated by asp-N digest with an N-terminal ten amino acid sequence of Aspartic Acid-Glycine-Aspartic acid-Asparagine-Phenylalanine-Proline-Leucine-Alanine-Proline-Phenylalanine (SEQ ID NO:1) as detailed in Example 8 here below. Further, the protein includes a peptide generated by cyanogen bromide cleavage with an N-terminal ten amino acid sequence of Lysine- Isoleucine- Alanine- Isoleucine- Glutamic acid- Alanine- Glycine- Tyrosine- Aspartic acid- Phenylalanine (SEQ ID NO:2) as detailed in Example 8 here below.

The isolated protein has a molecular weight of about 44,000–47,000 daltons as measured by SDS-PAGE. Further the protein binds specifically to a double stranded-DNA (ds-DNA) probe of sense and anti-sense oligonucleotides having the sense sequence:
5'----TAC-GAATGAAGTTGTGAAGCTGAGATTC-CCCTCC--- 3' (SEQ ID NO:3) and the anti-sense sequence
3'--------------CTTACTTCAACACTTCGACTCTAAGGG-GAGG-CAT--- 5' (SEQ ID NO:4), as detailed in Example 7 below. Microinjection into NIH-3T3 cells of the purified protein causes the induction of DNA synthesis in quiescent NIH-3T3 cells, as detailed in Example 9 below.

The DNA-binding protein (HPBF) is purified and isolated from tumor tissues using a ds-DNA probe of sense and anti-sense oligonucleotides having the sense sequence:
05'----TAC-GAATGAAGTTGTGAAGCTGAGATTC-CCCTCC---3' (SEQ ID NO:3) and the anti-sense sequence
3'--------------CTTACTTCAACACTTCGACTCTAAGGG-GAGG-CAT--- 5' (SEQ ID NO:4) as more fully detailed in Example 6.

This DNA-binding protein has been detected at high concentrations in samples of adenocarcinoma-admixed with carcinoma in situ of the breast, whereas the apparently benign breast tissue from the same quadrant area shows very minimal (almost unidentifiable) presence of this protein, and has also been found in the sera of patients with breast cancer, as detailed in Examples 2, 3 and 10. These studies indicate that this DNA-binding protein is specifically interacting with the promoter region of the ERBB2 gene during the transition of normal epithelial cells towards carcinoma in situ and subsequently to the development of invasive breast carcinoma and the protein is soluble and excreted into the serum. The protein, therefore, provides an earlier indication of transition to a cancerous state than the gene product of the ERBB2 gene itself.

The present invention also provides an antibody that is specifically reactive with HPBF. "Specifically reactive," as used herein describes an antibody or other ligand that specifically binds the HPBF protein and does not crossreact substantially with any antigen other than the HPBF protein. Antibody can include antibody fragments such as Fab fragments which retain the binding activity.

The antibody can be bound to a solid support substrate or conjugated with a detectable moiety or therapeutic compound or both bound and conjugated. Such conjugation techniques are well known in the art. For example, conjugation of fluorescent or enzymatic moieties can be performed as described in Johnstone & Thorpe, *Immunochemistry in Practice*, Blackwell Scientific Publications, Oxford, 1982.

The binding of antibodies to a solid support substrate is also well known in the art. (See, for example, Harlow and Lane, *Antibodies; A Laboratory Manual*, Cold Spring, Harbor Laboratory, Cold Spring Harbor, N.Y., 1988). The detectable moieties contemplated with the present invention can include fluorescent, enzymatic and radioactive markers. Therapeutic drugs contemplated with the present invention can include cytotoxic moieties such as ricin A chain, diphtheria toxin and chemotherapeutic compounds. Such therapeutic drugs can be utilized for killing cancer cells expressing HPBF.

Immunoassays

Immunoassays such as immunofluorescence assays, radioimmunoassays (RIA), immunoblotting and enzyme linked immunosorbent assays (ELISA) can be readily adapted to accomplish the detection of HBPF. In general, ELISAs are the preferred immunoassays employed to assess the amount of HBPF in a specimen. Both polyclonal and monoclonal antibodies can be used in the assays. An ELISA method effective for the detection of HBPF protein can, for example, be as follows: (1) bind the antibody to a substrate; (2) contact the bound antibody with a fluid or tissue sample containing the antigen; (3) contact the above with secondary antibody bound to a detectable moiety (e.g., horseradish peroxidase enzyme or alkaline phosphatase enzyme); (4) contact the above with the substrate for the enzyme; (5) contact the above with a color reagent; and (6) observe color change. Available immunoassays are extensively described in the patent scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; and 4,098,876.

Bioassays for Determining the Amount of HPBF in a Biological Sample

The present invention provides a method of determining the amount of HPBF in a biological sample comprising the steps of contacting the biological sample with a substance which binds HPBF under conditions such that a complex between HPBF and the substance can be formed and determining the amount of the complex, the amount of complex indicating the amount of HPBF in the sample.

As contemplated herein, a biological sample includes any body fluid which would contain the HPBF protein, such as blood, plasma, serum, and urineor any cell containing the HPBF protein. Examples of cells include tissues taken from surgical biopsies or isolated from a body fluid.

One example of the method of determining the amount of HPBF in a biological sample is performed by contacting the biological sample with a nucleic acid which binds HPBF under conditions to form a complex and determining the amount of HPBF/nucleic acid complex, the amount of the complex indicates the amount of HPBF in the sample. Nucleic acid sequences which bind HPBF to form a complex can be identified as described herein in the Examples. For example, the nucleic acid sequence of SEQ ID NO:3 binds HPBF as described herein.

Determination of the amount of HPBF/nucleic acid complex can be accomplished through techniques standard in the art. For example, the complex may be precipitated out of a solution or detected by the addition of a detectable moiety conjugated to the nucleic acid, as described, for example in Sambrook et al., *Molecular Cloning, A Laboratory Manual*, Cold Springs Harbor, N.Y., 1989).

Another example of the method of determining the amount of HPBF in a biological sample is performed by contacting the biological sample with an antibody against HPBF under conditions such that a specific complex of an antibody and HPBF can be formed and determining the amount of HPBF/antibody complex, the amount of the complex indicating the amount of HPBF in the biological sample. Antibodies which bind HPBF can be either monoclonal or polyclonal antibodies and can be obtained as described herein in the Examples. Determination of HPBF/antibody complexes can be accomplished using the immunoassays as described herein in the Examples.

The present invention also provides a method of detecting the presence of a cancer in a subject comprising determining the presence of a detectable amount of HPBF in a biopsy from the subject, the presence of a detectable amount of HPBF, relative to the absence of HPBF in a normal control, indicating the presence of a cancer. The method of determining the presence of a detectable amount of HPBF in a biopsy from the subject comprises the methods of determining the amount of HPBF in a biological sample as described herein in the Examples. As used herein, "biopsy" means any body fluids or cells which may contain HPBF which have been removed from the subject suspected of having a cancer. Also, as used herein, "detectable amount" means any amount of HPBF which is detectable by the methods of detection of HPBF described herein, as compared to the absence of a detectable amount of HPBF in a normal control biopsy taken from the same subject. When a normal biopsy sample and a suspected cancerous biopsy sample are removed from the same subject, any amount of HPBF present in the suspected sample, in greater quantities than an amount of HPBF detected in a normal sample, is considered a detectable amount. A detectable mount of HPBF is indicative of the presence of cancer, based on results of numerous studies as cited herein.

The present invention further provides a method of determining the prognosis of a subject having cancer comprising determining the presence of a detectable amount of HPBF in a biopsy from the subject, the presence of a detectable mount of HPBF, relative to the absence of HPBF in a normal control indicating a decreased chance of long-term survival. A detectable amount of HPBF is indicative of decreased chance of long-term survival based on the statistical correlations as described herein.

Isolation of DNA Encoding HPBF

The present invention provides an isolated nucleic acid encoding HPBF. By "isolated" is meant separated from other nucleic acids found in humans. The nucleic acid encoding HPBF is specific for humans expressing HPBF. By "specific" is meant an isolated sequence which does not hybridize with other nucleic acids to prevent an adequate hybridization with the nucleic acid encoding HPBF.

The isolated nucleic acid encoding HPBF can be obtained by standard methods well known in the art. For example, a library of cDNA clones can be generated and expressed in *E. coli* bacteria. Specific clones expressing HPBF or fragments thereof can be screened on colony blots using antibodies against HPBF generated as described in the Examples herein. Positive clones can then be sequenced by standard methods and the entire gene sequence of HPBF can be determined. (See, Sambrook et al., *Molecular Cloning; A Laboratory Manual*, Cold Springs Harbor, N.Y., 1989).

Also provided is an isolated nucleic acid that selectively hybridizes with the nucleic acid encoding HPBF under stringent conditions and has at least 70% and more preferably 80% and 90% complementarity with the segment and strand of the nucleic acid of HPBF to which it hybridizes. As used herein to deserve nucleic acids the term "selectively hybridizes" excludes the occasional randomly hybridizing nucleic acids as well as nucleic acids that encode other known promoter binding factors. Because the HPBF-encoding nucleic acid is double stranded, the selectively hybridizing nucleic acid can hybridize with either strand when the two strands of the coding sequence are not hybridized to each other. The selectively hybridizing nucleic acids can be used, for example, as probes or primers for detecting the presence of a sample that has a nucleic acid to which it hybridizes. Alternatively, the nucleic acid can encode a segment of the HPBF protein. The conditions of hybridization are stringent, but may vary depending on the length of the nucleic acids.

Modifications to the nucleic acids of the invention are also contemplated as long as the essential structure and function of the polypeptide encoded by the nucleic acids are maintained. Likewise, fragments used as primers or probes can have substitutions as long as enough complementary bases exist for selective hybridization (Kunkel et al., *Methods Enzymol.*, 154:367 (1987)).

Bioassays

The present invention provides a bioassay for screening substances for their ability to inhibit the activity of HPBF. Briefly, this can be accomplished by cotransfection assays whereby a plasmid containing a promoter gene, such as the bacterial chloramphenicolacetyltransferase (CAT) gene, cloned directly downstream of the ERBB2 promoter, can be cotransfected into a cultured cell line, such as COS7 cells, with a second plasmid which has a promoter known to be active in the cultured cells, cloned directly upstream of the HPBF gene. In such an assay, the HPBF gene encoding the HPBF transcript will be transcribing HPBF messenger RNA which will then be translated into HPBF protein. The HPBF protein then will be activating transcription of the reporter gene through its interaction with the ERBB2 promoter. The products of the reporter gene transcripts can then be quantitated. Such techniques for cotransfection and detection of CAT gene products in cultured cell lines are very well known in the art[98–101]. A cotransfected cell culture can then be contacted with compounds to screen them for the ability to inhibit the activity of HPBF. A compound which inhibits the activity of HPBF will inhibit the interaction of HPBF with the ERBB2 promoter. This decreased interaction is quantifiable by monitoring the CAT enzyme produced as a result of transcription directed by the ERBB2 promoter.

The present invention also provides a bioassay for screening substances for the ability to inhibit the mitogenic activity of HPBF in cultured NIH3T3 cells. NIH3T3 cells are highly sensitive to sarcoma virus formation and HPBF is known to produce mitogenic effect when introduced into these cells[102,103]. Briefly, quiescent NIH3T3 cultured cells are microinjected with HPBF and observed for any mitogenic effect, such as the formation of morphologically recognizable loci (cells no longer growing in an organized manner and as a monolayer, but contact inhibited and disorganized, eventually growing in disorganized multiple layers). Alternatively, DNA synthesis levels can be monitored both pre and post-injection as a direct measure of changes in genome replication[103].

Using this mitogenic assay, one can screen substances for their ability to inhibit the known mitogenic activity of HPBF. Such substances can be co-injected into quiescent NIH3T3 cells with HPBF and the mitogenic activity can then be compared to the mitogenic activity of HPBF or such substance injected alone. One can then readily determine whether a substance has an inhibitory effect on the mitogenic activity of HPBF.

Inhibition of Biological Activity of HPBF

The present invention provides a method of inhibiting a biological activity mediated by HPBF comprising preventing the HPBF from binding to the promoter region of the ERBB2 gene sequence.

In one example, the present invention provides a method of inhibiting a biological activity mediated by HPBF comprising preventing the HPBF from binding to the promoter region of the ERBB2 gene sequence wherein the binding to the promoter region is prevented by an antisense nucleotide sequence. The antisense oligonucleotide can be generated using well known nucleic acid synthesis methods as demonstrated in the Examples.

In another example, the present invention provides a method of inhibiting a biological activity mediated by HPBF comprising preventing the HPBF from binding to the promoter region of the ERBB2 gene sequence wherein the binding to the promoter region is prevented by a nongenomic nucleic acid sequence to which the HPBF binds.

A method to inhibit a biological activity of HPBF and decrease ERBB2 activity can use antisense or triplex oligonucleotide analogues or expression constructs. This entails introducing into the cell a nucleic acid sufficiently complementary in sequence so as to selectively hybridize to the target gene or message. Triplex inhibition relies on the transcriptional inhibition of the target gene and can be extremely efficient since only a few copies per cell are required to achieve complete inhibition. Antisense methodology on the other hand inhibits the normal processing, translation or half-life of the target message. Such methods are well known to one skilled in the art.

Although longer sequences can be used to achieve inhibition, antisense and triplex methods generally involve the treatment of cells or tissues with a relatively short oligonucleotide. The oligonucleotide can be either deoxyribo- or ribonucleic acid and must be of sufficient length to form a stable duplex or triplex with the target RNA or DNA at physiological temperatures and salt concentrations. It should also be of sufficient complementarity to selectively hybridize to the target nucleic acid. Oligonucleotide lengths sufficient to achieve this specificity are generally about 12 to 60 nucleotides long, preferably about 18 to 32 nucleotides long. In addition to length, hybridization specificity is also influenced by GC content and primary sequence of the oligonucleotide. Such principles are well known in the art and can be routinely determined by one who is skilled in the art.

The composition of the antisense or triplex oligonucleotides can also influence the efficiency of inhibition. For example, it is preferable to use oligonucleotides that are resistant to degradation by the action of endogenous nucleases. Nutlease resistance will confer a longer in vivo half-life onto the oligonucleotide and therefore increase its efficacy by reducing the required dose. Greater efficacy can also be obtained by modifying the oligonucleotide so that it is more permeable to cell membranes. Such modifications are well known in the art and include the alteration of the negatively charged phosphate backbone of the oligonucleotide to uncharged atoms such as sulfur and carbon. Specific examples of such modifications include oligonucleotides that contain methylphosphonate and thiophosphonate moieties in place of phosphate. These modified oligonucleotides can be applied directly to the cells or tissues to achieve entry into the cells and inhibition of HPBF activity. Other types of modifications exist as well and are known to one skilled in the art.

Recombinant methods known in the art can also be used to achieve the antisense or triplex inhibition of a target nucleic acid. For example, vectors containing antisense nucleic acids can be employed to express protein or antisense message to reduce the expression of the target nucleic acid and therefore its activity. Such vectors are known or can be constructed by those skilled in the art and should contain all expression elements necessary to achieve the desired transcription of the antisense or triplex sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found described in Sambrook et al., *Molecular Cloning: A Laboratory Manual*, Cold Springs Harbor Laboratory, N.Y. (1992), in Ausubel et al., *Current Protocols in Molecular Biology*, John Wiley and Sons, Baltimore, Md. (1989), and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the antisense vectors to specific cell types in vivo or within a tissue or mixed culture of cells. Viral vectors can also be modified with specific receptors or ligands to alter target specificity through receptor mediated events.

A specific example of a DNA viral vector for introducing and expressing antisense nucleic acids is the adenovirus derived vector Adenop53TK. This vector expresses a herpes virus thymidine kinase (TK) gene for either positive or negative selection and an expression cassette for desired recombinant sequences such as antisense sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or antisense sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which were not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on the desired cell type to be targeted. For example, if breast cancer is to be treated by decreasing the HPBF activity of cells affected by the disease, then a vector specific for such epithelial cells should be used. Likewise, if diseases or pathological conditions of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed though subsequent rounds of infection. The specific type of vector will depend upon the intended application. The actual vectors are also known and readily available within the art or can be constructed by one skilled in the art using well-known methodology.

HPBF antisense-encoding viral vectors can be administered in several ways to obtain expression and therefore decrease the activity of HPBF in cells affected by the disease or pathological condition. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into the spinal fluid can also be used as a mode of administration, especially in the case of neuro-degenerative diseases. Following injection, the viral vectors will circulate until they recognize host cells with the appropriate target specificity for infection.

An alternate mode of administration of HPBF antisense-encoding vectors can be by direct inoculation locally at the site of the disease or pathological condition or by inoculation into the vascular system supplying the tumor with nutrients. Local administration is advantageous because there is no dilution effect and, therefore, a smaller dose is required to achieve HPBF expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

In addition to the antisense methods described above, other methods can be used as well to decrease the activity of HPBF and achieve the down regulation of ERBB2 activity. For example, oligonucleotides which compete for the HPBF binding site within the ERBb2 regulatory elements can be used to competitively inhibit HPBF binding to ERBB2. Such oligonucleotides can be, for example, methylphosphonates and thiophosphonates which permeate the cell membrane. Alternatively, vectors which express such sequences or contain the HPBF binding element can also be used to achieve the same result as the oligonucleotides. Modes of administration for the competitive inhibition are similar to that described above for the antisense vectors and oligonucleotides.

The present invention also provides for a bioassay for screening substances for the ability to inhibit the production of HPBF comprising administering the substance to a cell having a gene activity expressing the HPBF gene (an activated gene encoding HPBF) and then determining the amount of HPBF subsequently produced.

Stably transformed cell lines expressing HPBF can be constructed in several ways. One example of such a technique is integrating genetic material known to encode HPBF into the chromosome of a host cell. Such integration, usually mediated through transfection of the DNA by DEAE Dextran, Calcium Phosphate precipitation, or via liposome encapsulation, can be coupled to the introduction of genes utilized to enhance gene expression. For example, the gene for the metabolic inhibitor, dihydrofolate reductase can be selected as the cotransfecting DNA to achieve DNA amplification and therefore enhanced or activated gene expression. In such a system, co-transfected cells are treated with methotrexate, a known inhibitor of dihydrofolate reductase. Cells resistant to methotrexate obtain this resistance by amplifying the numbers of dihydrofolate reductase genes. Genes other than the dihydrofolate gene are amplified as well [104].

Amplification of the cotransfected gene can be verified in several ways. These techniques can be, but are not limited to quantitative polymerase chain reaction, Southern blot hybridization, and dot blot hybridization. The presence of enhanced levels of HPBF protein can also be detected. One example of such a technique is through separating cellular proteins by polyacrylamide gel electrophoresis, either single or two dimensional, and then visualized by staining, or through antigen-antibody interaction. Such techniques are very well known in the art (Sambrook et al., *Molecular Cloning, A Laboratory Manual*, Cold Springs Harbor, N.Y., 1989).

Cells expressing HPBF can then be contacted with substances to screen for those which decrease the amount of HPBF produced. Techniques for detecting a change in the amount of HPBF produced can be, but are not limited to polyacrylamide gel electrophoresis, enzyme linked immunosorbent assay and by bioassay.

The invention will now be demonstrated by the following nonrestrictive examples:

The present invention is more particularly described in the following examples which are intended as illustrative only since numerous modifications and variations therein will be apparent to those skilled in the art.

EXAMPLES

GENERAL METHODS

Preparation of Cytoplasmic and Nuclear Extracts

The cytoplasmic and nuclear extracts from tissues and cells were prepared following standard procedures.[92] Briefly, cells were trypsinized ($1 \times 10^9$) and centrifuged at 5,500 rpm for 10 minutes. The supernatant was discarded and the pellet washed twice in 5× volume of phosphate buffered saline (PBS). Centrifugation step was repeated. The cell pellet was resuspended in 5× pellet volume of ice-cold buffer A (15 mM KCl, 10 mM Hepes, 2 mM $MgCl_2$, 0.1 mM EDTA). All remaining steps were performed at 4° C. The cells and tissues were homogenized using a glass-glass dounce homogenizer. The homogenization was complete when >85% of the cells were lysed as determined by phase contrast microscopy. The homogenate was mixed with 1/10 vol of buffer B (1M KCl, 50 mM Hepes, 30 mM $MgCl_2$, 0.1 mM EDTA, 1 mM DTT) and left on ice for 4–5 minutes followed by centrifugation at 10,000 rpm for 10 minutes. The supenatant was reserved for cytoplasmic extraction. The nuclear pellet was resuspended in 5 ml in a buffer of 9 parts buffer A and 1 part buffer B. Ammonium sulphate (4M, pH 7.9) was added to the extract to a final concentration of 0.36M and the nuclear proteins were extracted by gentle rocking on a shaker at 4° C. for 30 minutes. The DNA was separated from the proteins by centrifugation of the lysate at 150,000 g for 60 minutes. The supenatant was collected and the proteins were precipitated by the addition of 0.25 g ammonium sulphate per ml of supernatant. The precipitated proteins were collected by centrifugation at 150,000 g for 15 minutes and suspended in one-half of the original cell pellet volume in buffer C (10% Glycerol, 25 mM Hepes (pH 7.6), 40 mM KCl, 0.1 mM EDTA 1 mM DTT). The proteins were dialyzed against Buffer C for 2–4 hours, collected in a tube and centrifuged at 10,000 rpm for 10 minutes. Protein concentration was determined by Bio-Rad® protein reagents and the extract was stored in smaller aliquots at −70° C.

For cytoplasmic extraction of the reserved supernatant, 5 g of ammonium sulfate was added per 10 ml of supernatant and dissolved by gentle shaking at 4° C. The supernatant was then centrifuged the same way as for nuclear extract preparation. The precipitate was suspended in Buffer C and dialyzed against Buffer C as for nuclear extract preparation.

Preparation of Double Stranded Oligonucleotides

An aliquot of equal moles of sense and anti-sense oligonucleotides in $H_2O$ was mixed and the mixture was incubated sequentially at 95°–100° C. for 10 minutes, at 65° C. for 1 hour, 37° C. for 2–3 hours and at RT for 5 hours to form the double stranded (ds) oligonucleotides. The DNA was precipitated by the addition of 0.3M NaOAC and 2.5 vol of 100% ETOH. The precipitated DNA was collected by centrifugation and washed once with 70% ETOH and the pellet was dried under vacuum. The DNA was suspended in $H_2O$ and the exact concentration is determined by spectrophotometry.

5' End Labelling of Double Stranded Oligonucleotides

The 5' end labelling was accomplished essentially according to the manufacturer's protocol (Stratagene) using $\alpha$-$^{32}$P-ATP and the probe was purified through gel extraction. The labeled oligonucleotide was separated through an 8–10% PAGE in 1× TBE (Tris-borate-EDTA buffer). Loading of the samples was done by mixing with 5× dye.[93] Electrophoresis was continued at 30–36 mA for about 2–4 hours and the gel was exposed to Kodak® XAR-5 film and developed after about 10 minutes of exposure. The ds oligonucleotide band was cut from the gel, cut into smaller pieces and mixed with two volumes of a mixture containing 0.5M $NH_4OAC$ and 1 mM EDTA and allowed to shake at 370° C. overnight. The whole suspension was passed through glass wool in a 3 ml syringe and the clear radioactively labeled DNA solution was collected. Yeast tRNA to a final concentration of 30–40 μg/ml, was added to the labelled DNA and precipitated with 2.5 volume of ETOH overnight at −20° C. The tube was then centrifuged, the pellet washed once with 70% ETOH, and vacuum dried. The vacuum dried pellet was suspended in TE and the radioactivity was determined by counting an aliquot.

Gel Mobility Shift Assay (GMSA)

The tissue or cell extract was mixed with 5× binding buffer (125 mM HEPES, pH 7, containing 50 mM KCl, 5 mM DTT, 5 mM EDTA, 50% Glycerol and 0.25% NP-40), poly dI:dC (1–2 μg) and $H_2O$, and the mixture incubated at RT for 10 minutes in a reaction volume of 20–25 μl. The labelled probe (12,000–15,000 cpm) was then added to the mixture and the reaction was continued at RT for 40 minutes. At the end of the reaction time, 1 μl of 5× dye was added and loaded on a 6% pre-run PAGE in 1× TBE. The electrophoresis was continued at 32–36 mAmp. The gel was dried and exposed to the X-ray film.

Southwestern (DNA-Protein) Blot Assay

For the Southwestern procedure, the cytoplasmic or nuclear proteins were separated on SDS-PAGE (10% separating gel)[93] under reducing conditions and the proteins were electrotransferred onto nylon membrane (Immobilon® P membrane). The membrane was washed three times (one hour each) with renaturation buffer (10 mM Tris-Hcl, pH 7.5, 150 mM NaCl, 10 mM DTT, 2.5% NP-40, 10% Glycerol and 5% nonfat dry milk) and rinsed briefly in binding buffer (10 mM Tris-Hcl, pH 7.5, 40 mM NaCl, 1 mM DTT, 1 mM EDTA, 8% Glycerol and 0.125% non-fat dry milk). The membrane was then incubated in 15 ml of binding buffer plus 45 μg poly (dI-dC), 5 mM $MgCl_2$ and $1 \times 10^6$ cpm of $^{32}$P-labelled DNA probe per ml for 15 hours at RT with continuous agitation. The membrane was washed four times (30 minutes each) in 10 mM Tris-Hcl, pH 7.5 containing 50 mM NaCl and exposed to X-ray film.

Preparation of Sequence-Specific DNA-Sepharose Resin

Chemically synthesized complementary oligonucleotides (SEQ ID NO:3 AND SEQ ID NO:4) corresponding to −22 to +9 sequences (see Examples) of ERBB2 were annealed, 5'-phosphorylated, ligated and coupled to CNBr-activated sepharose 4B essentially according to the method of Kadonaga and Tjian.[94]

Affinity Purification of Sequence-Specific DNA-binding Protein

All operations were performed at 4° C. The oligonucleotide-affinity resin (1 ml) was equilibrated with buffer Z (0.1M KCl, 25 mM HEPES pH 7.6, 12.5 mM $MgCl_2$, 15% glycerol, 1 mM DTT and 0.05% NP-40). Cytoplasmic and/or nuclear extracts (10 ml) were dialyzed against buffer Z, combined with 250 μg of salmon sperm DNA and allowed to stand for 10 minutes on ice. This protein-DNA mixture was then mixed with the ERBB2-sepharose resin for 5–8 hours at 4° C. with occasional shaking and then loaded onto a column. The mixture was allowed to elute under gravity flow and washed with 4 to 5 column bed volumes of buffer Z. At this stage, the column was stopped, buffer Z containing 1M KCl (10 ml) was added and mixed with the resin thoroughly. The resin was allowed to stand for 15 minutes with occasional mixing and then the protein was eluted. This first cycle higher salt eluate was diluted in 0.1M KCl buffer Z, mixed with salmon sperm DNA and the whole procedure was repeated for second cycle purification identical to the first cycle.

Cell Lines and Primary Tumor Tissue

Cell lines NIH-3T3, (ATCC Accession No. CRL 1658) and SKBR3 (ATCC Accession No. HTB 30) were used. Primary breast cancer samples were obtained from mastectomy specimens. Pathology of each sample was confirmed using H&E stained frozen as well as formalin fixed tissue sections.

EXAMPLE 1

Preparation of Probes

In order to identify specific factor(s) that are responsible for the regulation of the ERBB2 gene, three sets of sense and anti-sense dsoligonucleotides based on the DNA sequence of a genomic clone of the ERBB2 promoter region entered in the Genbank were prepared. The promoter DNA sequence was analyzed through a Genbank data search.[21] The Genbank Accession numbers were M16789[95] and M16892[96]. The DNA sequences of these three sets of oligonucleotides are indicated below and a map is shown in FIG. 1.

The first sets were from base −79 to +9, relative to the last transcription start site (+1). The last transcription start site is located at position −178 relative to the first translational start codon "ATG". Therefore, the first set of oligonucleotides are from −258 to −169 relative to the first translational start codon "ATG". Position −178 is located at 21 bp downstream from the last TATAA box (−204 to −200 relative to the translational start codon). This set (Set 1, Probe C) of oligonucleotides consists of DNA sequences from the transcriptional start site, including TATAA and CAAT boxes. The second set (Set 2, Probe A) was from the same region, excluding TATAA and CAAT boxes (−79 to −22 relative to the transcriptional start site). The third set (Set 3, Probe B) of oligonucleotides was also from the same region excluding TATAA and CAAT boxes, but including transcriptional start site (−22 to +9), and including immediate base sequences upstream from the transcriptional start site, plus a few bases downstream of the transcriptional start site.

Set No. 1 to create probe C:

Sense Sequence: contains a three nucleotide 5' overhang.

5'----G C T -C C C A A T C A C A G G A G A A G G A G G A G G T G G A G G A G G A G G G C T G C T T G A G G A A G T A T A A G A A T G A A G T T G T G A A G C T G A G A T T C C C C T C C---3'(SEQ ID NO:5)

Antisense Sequence: contains a three nucleotide 5' overhang.

3'-------------G G G T T A G T G T C C T C T T C C T C C T C C A C C T C C T C C T C C C G A C G A A C T C C T T C A T A T T C T T A C T T C A A C A C T T C G A C T C T A A G G G G A G G- C A T---5' (SEQ ID NO:6)

Set No. 2 to create probe A:

Sense Sequence: contains a three nucleotide 5' overhang.

5'----G C T -C C C A A T C A C A G G A G A A G G A G G A G G T G G A G G A G G A G G G C T G C T T G A G G A A G T A T A A G A---3' (SEQ ID NO:7)

Antisense Sequence: contains a three nucleotide 5' overhang.

3'-------------G G G T T A G T G T C C T C T T C C T C C T C C A C C T C C T C C T C C C G A C G A A C T C C T T C A T A T T C T- C A T---5' (SEQ ID NO:8)

Set No. 3 to create probe B:

Sense Sequence: contains a three nucleotide 5' overhang.

5'----T A C -G A A T G A A G T T G T G A A G C T G A G A T T C C C C T C C---3' (SEQ ID NO:3)

Antisense Sequence: contains a three nucleotide 5' overhang.

3'-------------C T T A C T T C A A C A C T T C G A C T C T A A G G G G A G G- C A T---5' (SEQ ID NO:4)

The sequence and location of probe B is indicated in FIG. 1. The position for SP1 b binding sites and the classical CAAT and TATAA box is also indicated. All three sets of these oligonucleotide were used to generate double stranded DNA (ds-oligonucleotide).

EXAMPLE 2

Analysis by GMSA

Radioisotopically ($^{32}$P) labelled ds-oligonucleotide probes were made and Gel Mobility Shift Assays (GMSA) were carried out. For initial experiments, nuclear and cytoplasmic extracts were made from a benign specimen (normal) and a paired specimen of benign and tumor (adenocarcinoma admixed with carcinoma in situ), freshly collected from breast mastectomies, as well as SKRB3 cell extracts.

Nuclear and cytoplasmic extracts from a benign specimen and from a paired specimen of benign and tumor (pathologically diagnosed as adenocarcinoma) from the breast were analyzed by GMSA using all three probes. Probe B identified a specific factor which is present only in the nuclear and cytoplasmic extract of the tumor sample. The presence of this factor was totally absent in the nuclear extracts of benign tissue. However, the cytoplasmic extracts of both of the benign tissue samples show the presence of this factor at an extremely low level.

EXAMPLE 3

Further GMSA Analysis with Probe B

A series of four breast specimens of paired benign (B) and tumor (T) was analyzed similarly using GMSA and utilizing Probe B. The benign and tumor tissues were taken from the same quadrant area of the excised tissue. The histopathology examination identified the apparently benign area for use in the assay. Nuclear and cytoplasmic extracts from an atypical hyperplastic breast specimen were included.

These results clearly show the presence of a probe-B-specific binding factor in the tumor extracts of both nuclei and cytoplasm. The nuclear extracts of the apparently benign tissue from the same quadrant were completely devoid of this factor in this assay system. However, the cytoplasmic extracts of apparently benign and atypical hyperplastic tissue show the presence of this binding factor at a low level. It is not clear if the histopathologically apparently benign tissue from the same quadrant as the tumor is truly benign or whether it is in an early pre-cancerous stage which this assay recognizes. Similarly, HPBF has also been detected from cytoplasmic/nuclear extracts of a breast cancer cell line (SKBR3) known to overexpress ERBB2.

EXAMPLE 4

Binding Specificity of Factor

The binding specificity of the factor was confirmed with a sample which showed highest binding with probe B. Nuclear extracts of benign tissue were negative, whereas nuclear and cytoplasmic extracts of tumor specimens were positive for the Probe-B-binding factor. Binding of this factor with Probe B was completely abolished by excess unlabelled Probe B. This binding was not abolished using 50 fold unlabelled NFkB or SP1 probe, indicating that the binding of this factor is Probe-B-specific.

EXAMPLE 5

Determination of Factor as Protein

It was next determined that the binding factor (HPBF) is a protein. For this, the nuclear and cytoplasmic extracts were fractionated through SDS-polyacrylamide gel electrophoresis (SDS-PAGE). The proteins were transferred to nylon membrane and reacted with $^{32}$P-labelled probe B (Southwestern assay). Both the membranes show binding activity with probe B and probe A.

A protein of about 50 kDa can bind to probe B only with tumor cell extracts (nuclear and cytoplasmic). The nuclear and cytoplasmic extracts of benign tissue failed to show any signal in the Southwestern assay, indicating that the level of this DNA-binding protein is extremely low in apparently benign breast tissue.

EXAMPLE 6

Isolation and Purification of HPBF

Figure 2:
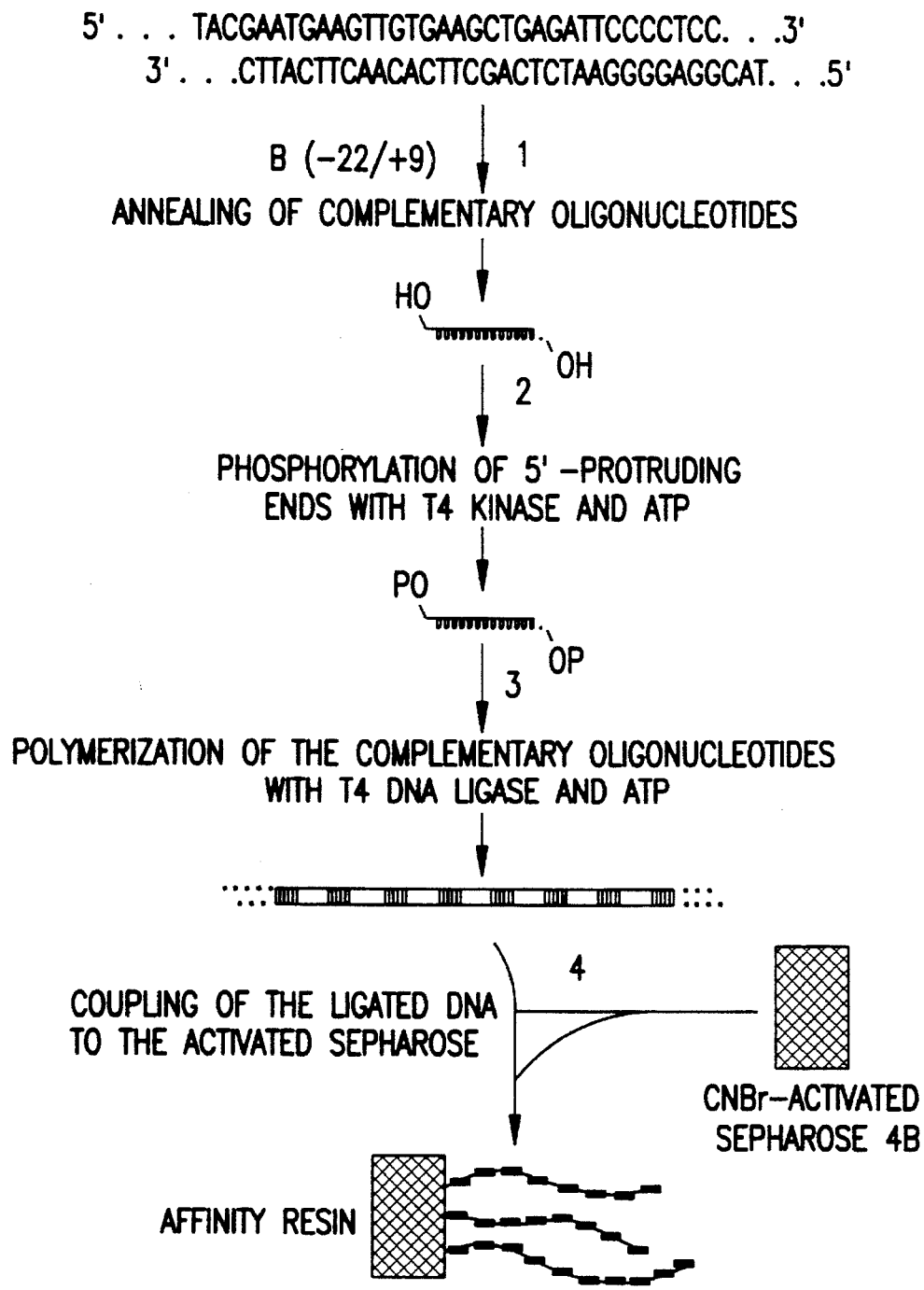
FIG. 2 presents the strategy used to construct specific DNA-sepharose resin using double stranded oligonucleotide (probe B) (SEQ ID NO:19).

In order to isolate and purify the probe-B-specific DNA-binding protein (HPBF), a strategy for the purification of DNA-binding protein was used. This strategy is diagramed in FIG. 2, using ds-oligonucleotide probe B to generate an affinity resin.

Pooled cytoplasmic extracts from three breast tumor specimens were subjected to the affinity purification. The extracts were passed through the affinity column and washed. The bound proteins were eluted with high salt buffer and three one milliliter fractions were collected. The proteins in the high salt eluate were fractionated through SDS-PAGE and silver-stained. The high salt wash in three fractions showed a specific protein at a very high concentration at around 44,000–47,000 dalton molecular weight. This again demonstrates the presence of a major protein, HPBF, of about 50 kDa as has been previously shown in the Southwestern assay. HPBF was dialyzed against GMSA binding buffer and stored in aliquots at −70° C.

EXAMPLE 7

Binding Specificity of Purified HPBF

The binding specificity of the purified HPBF was tested using GMSA and labelled probe B.

Only the tumor extract and purified HPBF bound DNA and formed a complex with probe B. The probe-B-specific binding protein is present in the tumor tissue specimen and the affinity purified protein. The benign extract did not show any binding. The specificity of the binding was competed out by unlabelled probe B, whereas a non-specific probe was unable to compete for the binding activity.

These results clearly document the identification of a protein factor (a DNA-binding protein), HPBF, which specifically binds to the promoter region of the ERBB2 gene sequences.

EXAMPLE 8

Amino Acid Sequence of Peptide of HPBF

An asp-N digest of the purified protein was performed following routine procedures well known to those skilled in the art. An N-terminal ten amino acid sequence of a peptide generated by the asp-N digest was determined using an automated protein micro sequencer. The ten amino acid sequence was determined to be Aspartic acid- Glycine- Aspartic acid-Asparagine- Phenylalanine- Proline- Leucine- Alanine- Proline- Phenylalanine (D G D N F P L A P F) (SEQ ID NO:1). It should be noted that the amino acid sequence of the protein may be slightly different due to possible sequencing errors. Such errors can be determined by repeating the methods to confirm sequence accuracy. The sequence was compared with known amino acid sequences in Genbank and no matches were found, indicating the novel nature of this peptide.

Further, a cyanogen bromide cleavage of the purified protein was performed following routine procedures well known to those skilled in the art. An N-terminal ten amino acid sequence of a peptide generated by the cyanogen bromide cleavage was determined using an automated protein micro sequencer. The ten amino acid sequence was determined to be Lysine- Isoleucine- Alanine- Isoleucine- Glutamic acid- Alanine- Glycine- Tyrosine-Aspartic acid- Phenylalanine (K I A I E A G Y D F) (SEQ ID NO:2). The sequence was compared with known amino acid sequences in Genbank and no match was found, indicating the novel nature of this peptide.

Therefore, these results indicate that HPBF (ERBB2 gene specific DNA-binding protein) is a newly discovered protein with known biological function, that has never been documented.

EXAMPLE 9

HPBF Induces Cell Proliferation

Purified and isolated HPBF was micro-injected into serum-starved NIH-3T3 cells as has been described in the scientific literature.[97]

Microinjection of HPBF into the quiescent NIH 3T3 cells induced the onset of DNA synthesis as detailed in TABLE 1 herein. DNA synthesis increased 12–13 fold with HPBF. The DNA synthesis was increased 28 fold in the presence of the Ras oncogene and HPBF, suggesting that the factor either has a mitogenic activity or is a component of mitogenic signalling pathways. The Ras oncogene was microinjected at an amount that gives minimal stimulation, as shown in Table I, since maximal stimulation as reported by Smith et al.[97] would not allow the HPBF response to be measured. Bovine serum albumin (BSA) was used as a control and showed, at most, a two-fold induction compared to the twelve to thirteen-fold increase induced by two separate extracts of HPBF. This induction of cell proliferation can be competed out slightly by incubating with probe B (ds-oligonucleotide 3), but not with nonspecific probe A (ds-oligonucleotide 2).

TABLE I

| Sample | % Injected Cells in S-Phase | Fold Induction |
| --- | --- | --- |
| BSA | 3 | 2(1) |
| HPBF extract 1 | 38 | 13(4) |
| HPBF extract 2 | 32 | 12(3) |
| HPBF-1 + Probe A | 25 | 9(3) |
| HPBF-1 + Probe B | 16 | 4(2) |
| c-Ras | 19 | 5(2) |
| HPBF-1 + c-Ras | 72 | 28(7) |

EXAMPLE 10

HPBF Can Be Measured in Sera

An ELISA assay of sera from breast, pancreas and kidney cancer patients against an anti-HPBF polyclonal antiserum demonstrated the presence of HPBF in the sera of breast cancer patients.

The polyclonal anti-HPBF sera were developed in hyperimmunized mice and were a pool of sera from three mice. The mice were being injected with purified and isolated HPBF for the production of monoclonal antibodies and the sera were obtained to determine the response of the immunized mice to the purified protein.

EXAMPLE 11

Production Of Polyclonal and Monoclonal Antibodies

Polyclonal antibodies against the human breast tumor-derived protein (HPBF) found in both nucleus and cytoplasm, were prepared by immunization of a NZW rabbit. The material used for immunization was purified from a crude nuclear extract by oligonucleotide affinity chromatography. The animal was injected with the purified protein emulsified with Freund's Complete Aduvant for the initial injection, then emulsified with Freund's Incomplete Aduvant for a second injection, and finally boosted with an injection of protein antigen in aqueous phase only. The animal was bled at weekly intervals and the serum analyzed for antibody activity using ELISA methodology with the purified antigen coated on the plate. The antiserum at peak development could be diluted >1:10,000 and still retain activity. Also, the antiserum was also used in a Western blot format to identify the antigen on a polyacrylamide gel at the correct molecular weight. This antibody retained activity after purification of the immunoglobulin by protein A-sepharose chromatography.

Monoclonal antibodies specifically reactive with HPBF protein were also prepared by immunizing a Balb/cAnnCr mouse with the affinity-purified protein after a further purification by cutting the specific band from a polyacrylamide gel. A similar immunization protocol was used, as described for polyclonal antibody production. After the mouse antiserum was shown to have antibody activity by ELISA testing, the animal was sacrificed and the spleen harvested. A spleen cell suspension was used to do a standard polyethylene glycol 1500 mediated-cell fusion with mouse myeloma 8.653 cells to form hybrids. Culture supernatants from the resulting cell hybridomas were screened for antibody activity using the same ELISA method. Antibody positive wells were cloned in two stages by limiting dilution to derive the present twenty-one clones that are being evaluated. All have antibody activity in the ELISA and some are Western blot positive as well. Purified antibody has been made from some of these clones, and some of these, as well as the polyclonal antibody react with breast cancer cells in immunohistochemical studies.

The invention has been described in an illustrative manner, and it is to be understood that the terminology which has been used is intended to be in the nature of words of description rather than of limitation.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

Throughout this application various publications are referenced by full citation or numbers. Full citations for the publications referenced by number are listed below. The disclosures of these publications in their entireties are hereby incorporated by reference into this application in order to more fully describe the state of the art to which this invention pertains.

REFERENCES

1. Go R. C. P., King M-C., Bailey-Wilson J., Elston R. D., Lynch H. T. Genetic epidemiology of breast cancer and associated cancers in high risk families. I. Segregation analysis. J. Natl. Cancer Inst. 71:455–461, 1983.
2. Goldstein A. M., Halle R. B. C., Hodge S. E., Paganini-Hill A., Spense M. A. Possible heterogeneity in the segregation pattern of breast cancer families with bilateral breast cancer. Genet. Epidemiol. 5:121–133, 1988.
3. Newman B., Austin M. A., Lee M., King M-C. Inheritance of human breast cancer: Evidence for autosomal dominant transmission in high-risk families. Proc. Natl. Acad. Sci. USA. 85:3044–3048, 1988.
4. Andrieu N., Clavel F., Demenais F. Familial susceptibility to breast cancer: A complex inheritance. Int. J. Cancer 44:415–418, 1989.
5. Anderson D. E. A genetic study of human breast cancer. J. Natl. Cancer Inst. 48:1029–34, 1972.
6. Anderson D. E. Genetic study of breast cancer. Ident. a high risk group. Cancer 34:1090–1097, 1974.
7. Anderson D. E. Breast cancer in families. Cancer 40:1855–1860, 1977.
8. Ottman R., King M-C., Pike M. C., Henderson B. E. Practical guide for estimating risk for familial breast cancer. Lancet 3:556–558, 1983.
9. Anderson D. E., Badzioch M. D. Risk of familial breast cancer. Cancer 56:383–387, 1985.
10. Cady B.: Familial bilateral cancer of the breast. Ann. Surg. 172:264–272, 1970.
11. Anderson D. E., Badzioch M. D.: Bilaterality in familial breast cancer patients. Cancer 56:2092–2098, 1985.
12. Sakamoto G., Sugano H., Kasumi F.: Bilateral breast cancer and familial aggregations. Prey. Med. 7:225–229, 1978.
13. Ponder B. A. J. Inherited predisposition to cancer. Trends in genetics 6:231–218, 1990.
14. Skolnick M. H., Cannon-Albright L. A., Goldgar D. E., Ward J. H., Marshall C. J., Schumann G. B., Hogle H., McWhorter W. P., Wright E. C., Tran T. D. Inheritance of proliferative breast disease in breast cancer kindreds. Science 250:1715–1720, 1990.
15. Wellings S. R., Jensen H. M. On the origin and progression of ductal carcinoma in the human breast. J. Natl. Cancer Inst. 50:1111–1118, 1973.
16. Malkin D., Li F. P., Strong L. C., Fraumeni J. F. Jr., Nelson C. E., Kim D. H., Kassel J., Gryka M. A., Bischoff F. Z., Tainsky M. A. Germ line p53 mutations in a familial syndrome of breast cancer, sarcomas, and other neoplasms. Science 250:1233–1238, 1990.
17. Srivastava S., Zou Z. Q., Pirollo K., Blattner W., Chang E. H. Germ-line transmission of a mutated p53 gene in a cancer-prone family with Li-Fraumeni syndrome. Nature 348:747–749, 1990.
18. Dickson R. B., Lippman M. E. Molecular determinants of growth, angiogenesis, and metastases in breast cancer. Seminars In Oneology 19:286–298, 1992.
19. Shih C., Padhy L. C., Murray M., Weinberg R. A. Transforming genes of carcinomas and neuroblastomas introduced into mouse fibroblasts. Nature 290:261–264, 1981.
20. Hung M. C., Schechter A. L., Chevray P. Y., Stern D. F., Weinberg R. A. Molecular cloning of the neu gene: absence of gross structural alteration in oncogenic alleles. Proc. Natl. Acad. Sci. USA. 83:261–264, 1986.
21. Coussens L., Yang-Feng T. L., Liao Y. C., Chen E., Gray A., McGrath J., Seeburg P. H., Liermann T. A. Schlessinger J., Francke U., Levinson A., Ullrich A. Tyrosine kinase receptor with extensive homology to EGF receptor shares chromosomal location with neu oncogene. Science 230:1132–1139, 1985.
22. Bargmann C. I., Hung M. C., Weinberg R. A. The neu oncogene encodes an epidermal growth factor receptor-related protein. Nature 319:226–230, 1986.
23. Yamamoto T., Ikawa S., Akiyama T., Semba K., Nomura N., Miyajima N., Saito T., Toyoshima K. Similarity of protein encoded by the human c-erb-B- 2 gene to epidermal growth factor receptor. Nature 319:230–234, 1986.
24. Lupu R., Colomer R., Zugmaier G., Sarup J., Shepard M., Slamon D., Lippman M. E. Direct interaction of a ligand for the erbB2 oncogene product with the EGF receptor and p185$^{erbB2}$. Science 249:1552–1255, 1990.
25. Wen D., Peles E., Cupples R., Suggs S. V., Bacus S. S., Luo Y., Trail G., Hu S., Silbiger S. M., Levy R. B., Kosaki R. A., Lu H. S., Yarden Y. Neu differentiation factor: a transmembrane glycoprotein containing an EGF domain and an immunoglobulin homology unit. Cell 69:559–572, 1992.
26. Holmes W. E., Sliwkowski M. X., Akita R. W., Henzel W. J., Lee J., Park J. W., Yansura D., Abadi N., Raab H., Lewis G. D., Shepard H. M., Kung W-J., Wood W. I., Goeddel D. V., Vandlen R. L. Identification of heregulin, a specific activator of p185$^{erbB2}$. Science 256:1205–1210, 1992.
27. Gusterson B. A., Machin L. G., Gullick W. J., Gibbs N. M., Powles T. J., Elliott C., Ashley S., Monaghan P., Harrison S. c-erbB-2 expression in benign and malignant breast disease. Br. J. Cancer 58:453–457, 1988.
28. van de Vijver M. J., Peterse J. L., Mooi W. J., Wisman P., Lomans J., Dalesio O., Nusse R. Neu-protein overexpression in breast cancer. Association with comedo-type ductal carcinoma in situ and limited prognostic value in stage II breast cancer. New Eng. J. Med. 319:1239–1245, 1988.
29. Ramachandra S., Machin L., Ashley S., Monaghan P., Custerson B. A. Immunohistochemical distribution of c-erbB-2 in in situ breast carcinoma—a detailed morphological analysis. J. Pathol. 161:7–14, 1990.
30. Lodato R., Maguire H. Jr., Greene M., Weiner D., LiVolsi V., Immunohistochemical Evaluation of c-erbB-2 Oncogene Expression in Ductal Carcinoma in situ and Atypical Ductal Hyperplasia of the Breast. Mod. Pathol. 3:449–454, 1990.
31. Bargmann C. I. and Weinberg R. A. Increased tyrosine kinase activity associated with protein encoded by the activated neu oncogene. Proc. Natl. Acad. Sci. U.S.A. 85:5394–5398, 1988.
32. Bargmann C. I., Hung M. C., Weinberg R. A. Multiple independent activations of the neu oncogene by a point mutation altering the transmembrane domain of p185. Cell 45:649–657, 1986.
33. Slamon D. J., Clark G. M., Wong S. G., Levin W. J., Ullrich A., McGuire W. L. Human breast cancer: correlation of relapse and survival with amplification of the HER-2/neu oncogene. Science 235:177–182, 1987.
34. Di Fiore P. P., Pierce J. H., Kraus M. H., Segatto O., King C. R., Aaronson S. A. erbB-2 is a potent oncogene when overexpressed in NIH/3T3 cells. Science 237:178–182, 1987.
35. King C. R., Kraus M. H., Aaronson S. A. Amplification of a novel v-erbB-related gene in a human mammary carcinoma. Science 229:974–976, 1985.

36. Kraus M. H., Popescu N. C., Amsbaugh S. C., King C. R. Overexpression of the EGF receptor-related proto-oncogene erbB-2 in human mammary tumor cell lines by different molecular mechanisms. EMBO J. 6:605–610, 1987.

37. van de Vijver M., van de Bersselaar R., Devilee P., Cornelisse C., Peterse J., Nusse R. Amplification of the neu (c-erbB-2) oncogene in human mammmary tumors is relatively frequent and is often accompanied by amplification of the linked c-erbA oncogene. Mol. Cell. Biol. 7:2019–2023, 1987.

38. Slamon D. J., Godolphin W., Jones L. A., Holt J. A., Wong S. G., Keith D. E., Levin W. J., Smart S. G., Udove J., Ullrich A., Press M. Studies of the HER-2/neu proto-oncogene in human breast and ovarian cancer. Science 244:707–712, 1989.

39. Suda Y., Aizawa S., Furuta Y., Yagi T., Ikawa Y., Saitoh K., Yamada Y., Toyoshima K., Yamamoto T. Induction of a variety of tumors by c-erbB2 and clonal nature of lymphomas even with the mutated gene ($Val^{659} \rightarrow Glu^{659}$). EMBO J. 9:181–190, 1990.

40. Muller W. J., Sinn E., Pattengale P. K., Wallace R., Leder P. Single-step induction of mammary adenocarcinoma in transgenie mice beating the activated c-neu oncogene. Cell 54:105–115, 1988.

41. Kern J. A., Schwartz D. A., Nordberg J. E., Weiner D. B., Greene M. I., Torney L., Robinson R. A. $p185^{neu}$ expression in human lung adenocarcinomas predicts shortened survival. Cancer Res. 50:5184–5191, 1990.

42. Shepard H. M., Lewis G. D., Sarup J. C., Fendly B. M., Maneval D., Mordenti J., Figari I., Kotts C. E., Palladino M. A. Jr., Ullrich A., Slamon D. Monoclonal antibody therapy of human cancer: taking the HER2 protooncogene to the clinic. J. Clin. Immunol. 11:117–127, 1991.

43. Toikkanen S., Helin H., Isola J., Joensuu H. Prognostic significance of HER-2 oncoprotein expression in breast cancer: a 30-year follow-up. J. Clin. Oncol. 10:1044–1048, 1992.

44. Perren T. J. c-erbB-2 oncogene as a prognostic marker in breast cancer. Br. J. Cancer 63:328–332, 1991.

45. Barnes D. M., Bartkova J., Camplejohn R. S., Gullick W. J., Smith P. J., Millis R. R. Overexpression of the c-erbB-2 oncoprotein: why does this occur more frequently in ductal carcinoma in situ than in invasive mammary carcinoma and is this of prognostic significance? Eur. J. Cancer 28:644–648, 1992.

46. Ali I. U., Cambell G., Lidereau R., Callahan R. Lack of evidence for the prognostic significance of c-erbB2 amplification in human breast cancer. Oncogene Res. 3:139–146, 1988.

47. Bartkova J., Barnes D. M., Millis R. R., Gullick W. J. Immunohistochemical demonstration of c-erbB-2 protein in mammary ductal carcinoma in situ. Hum. Pathol. 21:1164–1167, 1990.

48. Barnes D. M., Lammie G. A., Millis R. R., Gullick W. J., Allen D. S., Altman D. G. An immunohistochemical evaluation of c-erbB2 expression in human breast carcinoma. Br. J. Cancer 58:448–452, 1988.

49. Borg A., Linell F., Idvall I., Johansson S., Sigurdsson H., Ferno M., Killander D. HER2/neu amplification and comedo type breast carcinoma. Lancet 1:1268–1269, 1989.

50. Iglehart J. D., Kraus M. H., Lagton B. C., Huper G., Kerns B. J., Marks J. R. Increased erbB2 gene copies and expression in multiple stages of breast cancer. Cancer Res. 50:6701–6707, 1990.

51. Barnes D. M., Meyer J. S., Gonzalez J. G., Gullick W. J., Millis R. R. Relationship between c-erbB-2 immunoreactivity and thymidine labelling index in breast carcinoma in situ. Breast Cancer Res. Treat. 18:11–17, 1991.

52. Meyer J. S. Cell kinetics of histological variants of in situ breast carcinoma. Breast Cancer Res. Treat. 7:171–180, 1986.

53. Hardman P. D., Worth A., Lee U., Baird R. M. The risk of occult invasive breast cancer after excisional biopsy showing in situ ductal carcinoma of comedo pattern [published erratum] Canadian J. Surgery. 32:56–60, 1989.

54. Schwartz G. F., Patchefsky A. S., Finkelstein S. D. Non-palpable in situ ductal carcinoma of the breast. Arch. Surg. 124:29–32, 1989.

55. Lagios M., Margolin F. R., Westdhal P. R. Mammographically detected duct carcinoma in situ: Frequency of local recurrence following tylectomy and prognostic effect of nuclear grade on local recurrence. Cancer 63:618–624, 1989.

56. Gusterson, B. A., Gelber R. D., Goldhirsch A., Price K. N., Save-Soderborgh J., Anbazhagan R. Prognostic importance of c-erbB2 expression in breast cancer. J. Clin. Oncol. 10:1049–1056, 1992.

57. Margaret R., White A., Hung M-C. Cloning and characterization of the mouse neu promoter. Oncogene 7:677–683, 1992.

58. Ishi K., Horiuchi H., Miyazaki Y., Tani T., Yagi Y., Saito S. Detection of estrogen receptors in human breast tumors by immunocytochemical assay (ER-ICA). Jap. J. Clin. Pathol. 35:1239–1244, 1987.

59. Suen T. C., Hung M-C. Multiple cis- and trans-acting elements involved in regulation of the neu gene. Mol. Cell. Biol. 10:6306–6315, 1990.

60. Kageyama R., Pastan I. Molecular cloning and characterization of a human DNA-binding factor that represses transcription. Cell 59:815–829, 1989.

61. Singh H., Sen R., Baltimore D., Sharp P. A. A nuclear factor that binds to a conserved sequence motif in transcriptional control elements of immunoglobulin genes. Nature 319:154–158, 1986.

62. Fletcher C., Heintz N., Roeder R. G. Purification and characterization of OTF-1, a transcription factor regulating cell cycle expression of a human histone H2b gene. Cell 51:773–781, 1987.

63. Imagawa M., Chiu R., Karin M. Transcription factor AP-2 mediates induction by two different signal-transduction pathways: protein kinase C and cAMP. Cell 51:251–260, 1987.

64. Yan D-H., Hung M-C. Identification and characterization of a novel enhancer for the rat neu promoter. Mol. Cell. Biol. 11:1875–1882, 1991.

65. Kokai Y., Cohen J. A., Drebin J. A., Greene M. I. Stage and tissue specific expression of the neu oncogene in rat development. Proc. Natl. Acad. Sci. USA. 84:8498–8501, 1987.

66. Capecchi M. R. Altering the genome by homologous recombination. Science 244:1288–1292, 1989.

67. Hunter T., Karin M. The Regulation of Transcription by Phosphorelation. Cell 70:375–387, 1992.

68. Bohmann D. Transcription factor phosphorylation: a link between signal transduction and the regulation of gene expression. Cancer Cells 2:337–343, 1990.

69. Allred et al. Overexpression of HER-2/neu and Its Relationship with Other Prognostic Factors Change During the Progression of in situ to Invasive Breast Cancer, Human Pathology 23(9):974–979, 1992

70. Russell, K. S. and Hung, M-C. Transcriptional Repression of the neu Protooncogene by Estrogen Stimulated Estrogen Receptor. Cancer Research 52:6624–6629, 1992

71. Wells et al. Selective Inhibition of Tumor Cell Growth by a Recombinant Single-Chain Antibody-Toxin Specific for the erbB-2 Receptor, Cancer Research 52:6310–6317, 1992

72. Rihs H-P., Jans D. A., Fan H., Peters R. The rate of nuclear cytoplasmic protein transport is determined by the casein kinase II site flanking the nuclear localization sequence of the SV40 T-antigen. EMBO J. 10:633–639, 1991.

73. Baeuerle P. A., Baltimore D. Activation of DNA-binding activity in an apparently cytoplasmic precursor of the NF-χB transcription factor. Cell 53:211–217, 1988.

74. Baeuerle P. A., Baltimore D. IχB: a specific inhibitor of the NF-χB transcription factor. Science 242:540–546, 1988.

75. Yan D-H., Chang L-S., Hung M-C. Repressed expression of the Her-2-neu/C-erbB-2 protooncogene by the adenovirus E1A gene products. Oncogene 6:343–345, 1991.

76. Knudson A. G. Jr. Retinoblastoma: A prototypic hereditary neoplasm. Seminars in Ontology 5:57–60, 1978.

77. Horowitz J. M., Park S. H., Bogenmann E., Cheng J. C., Yandell D. W., Kaye F. J., Minna J. D., Dryja T. P., Weinberg R. A. Frequent inactivation of the retinoblastoma anti-oncogene is restricted to a subset of human tumor cells. Proc. Natl. Acad. Sci. USA. 87:2775–2779, 1990.

78. Chen P. L., Scully P., Shew J. Y., Wang J. Y., Lee W. H. Phosphorylation of the retinoblastoma gene product is modulated during the cell cycle and cellular differentiation. Cell 58:1193–1198, 1989.

79. Ludlow J. W., Shon J., Pipas J. M., Livingston D. M., DeCaprio J. A. The retinoblastoma susceptibility gene product undergoes cell cycle dependent dephosphorylation and binding to and release from SV40 large T. Cell 60:387–396, 1990.

80. Lin B. T., Gruenwald S., Morla A. O., Lee W. H., Wang J. Y. Retinoblastoma cancer suppressor gene product is a substrate of the cell cycle regulator cdc2 kinase. EMBO J. 10:857–864, 1991.

81. Wagner S., Green M. R. Retinoblastoma. A transcriptional tryst. Nature 352:189–190, 1991.

82. Bandara L. R., Adamczewski J. P., Hunt T., La Thangue N. B. Cyclin A. and the retinoblastoma gene product complex with a common transcription factor. Nature 352:249–251, 1991.

83. Robbins P. D., Horowitz J. M., Mulligan R. C. Negative regulation of human c-fos expression by the retinoblastoma gene product. Nature 346:668–671, 1990.

84. Kim S. J., Lee H. D., Robbins P. D., Busam K., Sporn M. B., Roberts A. B. Regulation of transforming growth factor β1 gene expression by the product of the retinoblastoma-susceptibility gene. Proc. Natl. Acad. Sci. USA. 88:3052–3056, 1991.

85. Schneider P. M., Hung M. C., Chiocca S. M., Manning J., Zhao X. Y., Fang K., Roth J. A. Differential expression of the c-erbB-2 gene in human small cell and non-small cell lung cancer. Cancer Res. 49:4968–4971, 1989.

86. Lee E. Y., To H., Shew J. Y., Bookstein R., Scully P., Lee W. H. Inactivation of the retinoblastoma susceptibility gene in human breast cancers. Science 241:218–221, 1988.

87. Yu D., Matin A., Hung M-C. The retinoblastoma gene product suppresses neu oncogene-induced transformation via transcriptional repression of neu. J. Biol. Chem. 267:10203–10206, 1992.

88. Breathnach R., Chambon P. Organization and expression of eucaryotic split genes coding for proteins. Annual Review of Biochemistry 50:349–383, 1981.

89. Jones K. A., Yamamoto K. R., Tjian R. Two distinct transcription factors bind to the HSV thymidine kinase promoter in vitro. Cell 42:559–572, 1985.

90. Graves B. J., Johnson P. F., McKnight S. L. Homologous recognition of a promoter domain common to the MSV LTR and the HSV tk gene. Cell 44:565–576, 1986.

91. Miyamoto N. G., Moncollin V., Wintzerith M., Hen R., Egly J. M., Chambon P. Stimulation of in vitro transcription by the upstream element of the adenovirus-2 major late promoter involves a specific factor. Nucl. Acid Res. 12:8779–8799, 1984.

92. Parker C. S. and Topal J., A Drosophila RNA Polymerase II Transcription Factor Contains a Promoter-Region-Specific DNA-Binding Activity, Cell 36:357, 1984.

93. Sambrook, T. et al., *Molecular Cloning: A laboratory manual*, 2nd Edition, Cold Spring Harbor Laboratory, Cold Spring Harbor, N.Y., pp. 6.3–6.19; 6.36–6.45; and 18.47–18.63, 1989.

94. Kadonaga J. T., Tjian R. Affinity Purification of sequence-specific DNA binding Proteins. Proc. Natl. Acad. Sci. U.S.A., 83:5889–5893, 1986.

95. Tal, M. et al., "Human HER2 (neu) Promoter: Evidence for Multiple Mech. for Transcriptional Initiation", Mol. Cell. Biol. 7:2597–2601, 1987.

96. Ishii, S. et al., "Characterization of the Promoter Region of the Human cerbB-2 Protooncogene", Proc. Natl. Acad. Sci. USA, 84:4374–4378, Jul. 1987.

97. Smith, M. R., et al., Translation Initiation Factors Induce DNA Synthesis and Transform NIH 3T3 Cells, New Biologist, 2:648–654, 1990.

98. Gluzman, Y., Cell, 23:175–182, 1981.

99. Felgner, P. et. al., Proc. Natl. Acad. Sci., 84:7413–7417, 1987.

100. Shigckam, K. et al., BioTechniques, 6:742–751, 1988.

101. Sovthern, P. J. et al., J. Mol. App. Gen., 1:327–342, 1982.

102. Smith, M. R. et al., New Biol., 2:648–654, 1990.

103. Sarkar, F. H., et al., J. Biol. Chem., pp. 1–5, 1994.

104. Watson, J. D. et al., Rcombinant DNA 2nd Ed., 1992.

---

What is claimed is:

1. A method of detecting the presence of a cancer correlated with the presence of Her-2/neu promoter binding factor, in a subject comprising determining the presence of a detectable amount of Her-2/neu promoter binding factor in a biological sample from the subject, the presence of a detectable amount of Her-2/neu promoter binding factor relative to the absence of Her-2/neu promoter binding factor in a normal control indicating the presence of a cancer correlated with the presence of Her-2/neu promoter binding factor.

2. A method of determining the prognosis of a subject having a cancer correlated with the presence of Her-2/neu promoter binding factor, comprising determining the presence of a detectable amount of Her-2/neu promoter binding factor in a biological sample from a subject, the presence of a detectable amount of Her-2/neu promoter binding factor relative to the absence of Her-2/neu promoter binding factor in a normal control indicating a decreased chance of long term survival.

3. The method of claim 1, wherein the presence of a detectable amount of Her-2/neu promoter binding factor is determined by a) contacting the biological sample with a nucleic acid to which the HPBF binds under conditions such that an HPBF/nucleic acid complex can be formed; and b) detecting the formation of the HPBF/nucleic acid complex, the formation of the complex indicating the presence of HPBF in the biological sample.

4. The method of claim 3, wherein the nucleic acid is the nucleic acid set forth in SEQ ID NO:3.

5. The method of claim 1, wherein the presence of a detectable amount of Her-2/neu promoter factor is determined by a) contacting the biological sample with an antibody which specifically binds HPBF under conditions such that an HPBF/antibody complex can be formed; and b) detecting the formation of the HPBF/antibody complex, the formation of the complex indicating the presence of HPBF in the biological sample.

6. The method of claim 5, wherein the antibody is conjugated to a detectable moiety.

7. The method of claim 6, wherein the antibody is bound to a solid support.

8. The method of claim 2, wherein the presence of a detectable amount of Her-2/neu promoter binding factor is determined by a) contacting the biological sample with a nucleic acid to which the Her-2/neu promoter binding factor binds under conditions such that an Her-2/neu promoter binding factor/nucleic acid complex can be formed; and b) detecting the formation of the Her-2/neu promoter binding factor/nucleic acid complex, the formation of the complex indicating the presence of Her-2/neu promoter binding factor in the biological sample.

9. The method of claim 8, wherein the nucleic acid is the nucleic acid set forth in SEQ ID NO:3.

10. The method of claim 2, wherein the presence of a detectable amount of Her-2/neu promoter binding factor is determined by a) contacting the biological sample with an antibody which specifically binds Her-2/neu promoter binding factor under conditions such that an Her-2/neu promoter binding factor/antibody complex can be formed; and b) detecting the formation of the Her-2/neu promoter binding factor/antibody complex, the formation of the complex indicating the presence of Her-2/neu promoter binding factor in the biological sample.

11. The method of claim 10, wherein the antibody is conjugated to a detectable moiety.

12. The method of claim 10, wherein the antibody is bound to a solid support.

13. The method of claim 1, wherein the cancer is breast cancer.

14. The method of claim 2, wherein the cancer is breast cancer.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
      ( A ) LENGTH: 10 amino acids ( B ) TYPE: amino acid
( C ) STRANDEDNESS: single
( D ) TOPOLOGY: linear ( x i ) SEQUENCE DESCRIPTION: SEQ ID NO:1:

```
Asp Gly Asp Asn Phe Pro Leu Ala Pro Phe
1               5                   10
```

( 2 ) INFORMATION FOR SEQ ID NO:2:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( x i ) SEQUENCE DESCRIPTION: SEQ ID NO:2:

```
Lys Ile Ala Ile Glu Ala Gly Tyr Asp Phe
1               5                   10
```

( 2 ) INFORMATION FOR SEQ ID NO:3:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:3:

TACGAATGAA GTTGTGAAGC TGAGATTCCC CTCC                                    34

( 2 ) INFORMATION FOR SEQ ID NO:4:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:4:

CTTACTTCAA CACTTCGACT CTAAGGGGAG GCAT                                    34

( 2 ) INFORMATION FOR SEQ ID NO:5:

( i ) SEQUENCE CHARACTERISTICS:
( A ) LENGTH: 89 base pairs
( B ) TYPE: nucleic acid
( C ) STRANDEDNESS: single
( D ) TOPOLOGY: linear ( x i ) SEQUENCE DESCRIPTION: SEQ ID NO:5:

GCTCCCAATC ACAGGAGAAG GAGGAGGTGG AGGAGGAGGG CTGCTTGAGG AAGTATAAGA        60

ATGAAGTTGT GAAGCTGAGA TTCCCCTCC                                          89

( 2 ) INFORMATION FOR SEQ ID NO:6:

( i ) SEQUENCE CHARACTERISTICS:
( A ) LENGTH: 89 base pairs
( B ) TYPE: nucleic acid
( C ) STRANDEDNESS: single
( D ) TOPOLOGY: linear ( x i ) SEQUENCE DESCRIPTION: SEQ ID NO:6:

GGGTTAGTGT CCTCTTCCTC CTCCACCTCC TCCTCCCGAC GAACTCCTTC ATATTCTTAC        60

TTCAACACTT CGACTCTAAG GGGAGGCAT                                          89

( 2 ) INFORMATION FOR SEQ ID NO:7:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
GCTCCCAATC ACAGGAGAAG GAGGAGGTGG AGGAGGAGGG CTGCTTGAGG AAGTATAAGA    60
```

( 2 ) INFORMATION FOR SEQ ID NO:8:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
GGGTTAGTGT CCTCTTCCTC CTCCACCTCC TCCTCCCGAC GAACTCCTTC ATATTCTCAT    60
```

( 2 ) INFORMATION FOR SEQ ID NO:9:

( i ) SEQUENCE CHARACTERISTICS:
        ( A ) LENGTH: 4530 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
AATTCTCGAG CTCGTCGACC GGTCGACGAG CTCGAGGGTC GACGAGCTCG AGGGCGCGCG      60
CCCGGCCCCC ACCCCTCGCA GCACCCCGCG CCCCGCGCCC TCCAGCCGG  GTCCAGCCGG     120
AGCCATGGGG CCGGAGCCGC AGTGAGCACC ATGGAGCTGG CGGCCTTGTG CCGCTGGGGG     180
CTCCTCCTCG CCCTCTTGCC CCCCGGAGCC GCGAGCACCC AAGTGTGCAC CGGCACAGAC     240
ATGAAGCTGC GGCTCCCTGC CAGTCCCGAG ACCCACCTGG ACATGCTCCG CCACCTCTAC     300
CAGGGCTGCC AGGTGGTGCA GGGAAACCTG GAACTCACCT ACCTGCCCAC CAATGCCAGC     360
CTGTCCTTCC TGCAGGATAT CCAGGAGGTG CAGGGCTACG TGCTCATCGC TCACAACCAA     420
GTGAGGCAGG TCCCACTGCA GAGGCTGCGG ATTGTGCGAG GCACCCAGCT CTTTGAGGAC     480
AACTATGCCC TGGCCGTGCT AGACAATGGA GACCCGCTGA ACAATACCAC CCCTGTCACA     540
GGGGCCTCCC CAGGAGGCCT GCGGGAGCTG CAGCTTCGAA GCCTCACAGA GATCTTGAAA     600
GGAGGGGTCT TGATCCAGCG GAACCCCCAG CTCTGCTACC AGGACACGAT TTTGTGGAAG     660
GACATCTTCC ACAAGAACAA CCAGCTGGCT CTCACACTGA TAGACACCAA CCGCTCTCGG     720
GCCTGCCACC CCTGTTCTCC GATGTGTAAG GGCTCCCGCT GCTGGGGAGA GAGTTCTGAG     780
GATTGTCAGA GCCTGACGCG CACTGTCTGT GCCGGTGGCT GTGCCCGCTG CAAGGGGCCA     840
CTGCCCACTG ACTGCTGCCA TGAGCAGTGT GCTGCCGGCT GCACGGGCCC CAAGCACTCT     900
GACTGCCTGG CCTGCCTCCA CTTCAACCAC AGTGGCATCT GTGAGCTGCA CTGCCCAGCC     960
CTGGTCACCT ACAACACAGA CACGTTTGAG TCCATGCCCA ATCCCGAGGG CCGGTATACA    1020
TTCGGCGCCA GCTGTGTGAC TGCCTGTCCC TACAACTACC TTTCTACGGA CGTGGGATCC    1080
TGCACCCTCG TCTGCCCCCT GCACAACCAA GAGGTGACAG CAGAGGATGG AACACAGCGG    1140
TGTGAGAAGT GCAGCAAGCC CTGTGCCCGA GTGTGCTATG GTCTGGGCAT GGAGCACTTG    1200
CGAGAGGTGA GGGCAGTTAC CAGTGCCAAT ATCCAGGAGT TTGCTGGCTG CAAGAAGATC    1260
TTTGGGAGCC TGGCATTTCT GCCGGAGAGC TTTGATGGGG ACCCAGCCTC CAACACTGCC    1320
```

| | | | | | |
|---|---|---|---|---|---|
| CCGCTCCAGC | CAGAGCAGCT | CCAAGTGTTT | GAGACTCTGG | AAGAGATCAC | AGGTTACCTA | 1380 |
| TACATCTCAG | CATGGCCGGA | CAGCCTGCCT | GACCTCAGCG | TCTTCCAGAA | CCTGCAAGTA | 1440 |
| ATCCGGGGAC | GAATTCTGCA | CAATGGCGCC | TACTCGCTGA | CCCTGCAAGG | GCTGGGCATC | 1500 |
| AGCTGGCTGG | GGCTGCGCTC | ACTGAGGGAA | CTGGGCAGTG | GACTGGCCCT | CATCCACCAT | 1560 |
| AACACCCACC | TCTGCTTCGT | GCACACGGTG | CCCTGGGACC | AGCTCTTTCG | GAACCCGCAC | 1620 |
| CAAGCTCTGC | TCCACACTGC | CAACCGGCCA | GAGGACGAGT | GTGTGGGCGA | GGGCCTGGCC | 1680 |
| TGCCACCAGC | TGTGCGCCCG | AGGGCACTGC | TGGGGTCCAG | GGCCCACCCA | GTGTGTCAAC | 1740 |
| TGCAGCCAGT | TCCTTCGGGG | CCAGGAGTGC | GTGGAGGAAT | GCCGAGTACT | GCAGGGGCTC | 1800 |
| CCCAGGGAGT | ATGTGAATGC | CAGGCACTGT | TTGCCGTGCC | ACCCTGAGTG | TCAGCCCCAG | 1860 |
| AATGGCTCAG | TGACCTGTTT | TGGACCGGAG | GCTGACCAGT | GTGTGGCCTG | TGCCCACTAT | 1920 |
| AAGGACCCTC | CCTTCTGCGT | GGCCCGCTGC | CCAGCGGTG | TGAAACCTGA | CCTCTCCTAC | 1980 |
| ATGCCCATCT | GGAAGTTTCC | AGATGAGGAG | GGCGCATGCC | AGCCTTGCCC | CATCAACTGC | 2040 |
| ACCCACTCCT | GTGTGGACCT | GGATGACAAG | GGCTGCCCCG | CCGAGCAGAG | AGCCAGCCCT | 2100 |
| CTGACGTCCA | TCGTCTCTGC | GGTGGTTGGC | ATTCTGCTGG | TCGTGGTCTT | GGGGGTGGTC | 2160 |
| TTTGGGATCC | TCATCAAGCG | ACGGCAGCAG | AAGATCCGGA | AGTACACGAT | GCGGAGACTG | 2220 |
| CTGCAGGAAA | CGGAGCTGGT | GGAGCCGCTG | ACACCTAGCG | GAGCGATGCC | CAACCAGGCG | 2280 |
| CAGATGCGGA | TCCTGAAAGA | GACGGAGCTG | AGGAAGGTGA | AGGTGCTTGG | ATCTGGCGCT | 2340 |
| TTTGGCACAG | TCTACAAGGG | CATCTGGATC | CCTGATGGGG | AGAATGTGAA | AATTCCAGTG | 2400 |
| GCCATCAAAG | TGTTGAGGGA | AAACACATCC | CCCAAAGCCA | ACAAAGAAAT | CTTAGACGAA | 2460 |
| GCATACGTGA | TGGCTGGTGT | GGGCTCCCCA | TATGTCTCCC | GCCTTCTGGG | CATCTGCCTG | 2520 |
| ACATCCACGG | TGCAGCTGGT | GACACAGCTT | ATGCCCTATG | GCTGCCTCTT | AGACCATGTC | 2580 |
| CGGGAAAACC | GCGGACGCCT | GGGCTCCCAG | GACCTGCTGA | ACTGGTGTAT | GCAGATTGCC | 2640 |
| AAGGGGATGA | GCTACCTGGA | GGATGTGCGG | CTCGTACACA | GGGACTTGGC | CGCTCGGAAC | 2700 |
| GTGCTGGTCA | AGAGTCCCAA | CCATGTCAAA | ATTACAGACT | TCGGGCTGGC | TCGGCTGCTG | 2760 |
| GACATTGACG | AGACAGAGTA | CCATGCAGAT | GGGGGCAAGG | TGCCCATCAA | GTGGATGGCG | 2820 |
| CTGGAGTCCA | TTCTCCGCCG | GCGGTTCACC | CACCAGAGTG | ATGTGTGGAG | TTATGGTGTG | 2880 |
| ACTGTGTGGG | AGCTGATGAC | TTTTGGGGCC | AAACCTTACG | ATGGGATCCC | AGCCCGGGAG | 2940 |
| ATCCCTGACC | TGCTGGAAAA | GGGGGAGCGG | CTGCCCCAGC | CCCCCATCTG | CACCATTGAT | 3000 |
| GTCTACATGA | TCATGGTCAA | ATGTTGGATG | ATTGACTCTG | AATGTCGGCC | AAGATTCCGG | 3060 |
| GAGTTGGTGT | CTGAATTCTC | CCGCATGGCC | AGGGACCCCC | AGCGCTTTGT | GGTCATCCAG | 3120 |
| AATGAGGACT | TGGGCCCAGC | CAGTCCCTTG | GACAGCACCT | TCTACCGCTC | ACTGCTGGAG | 3180 |
| GACGATGACA | TGGGGGACCT | GGTGGATGCT | GAGGAGTATC | TGGTACCCCA | GCAGGGCTTC | 3240 |
| TTCTGTCCAG | ACCCTGCCCC | GGGCGCTGGG | GCATGGTCC | ACCACAGGCA | CCGCAGCTCA | 3300 |
| TCTACCAGGA | GTGGCGGTGG | GGACCTGACA | CTAGGGCTGG | AGCCCTCTGA | AGAGGAGGCC | 3360 |
| CCCAGGTCTC | CACTGGCACC | CTCCGAAGGG | GCTGGCTCCG | ATGTATTTGA | TGGTGACCTG | 3420 |
| GGAATGGGGG | CAGCCAAGGG | GCTGCAAAGC | CTCCCCACAC | ATGACCCCAG | CCCTCTACAG | 3480 |
| CGGTACAGTG | AGGACCCCAC | AGTACCCCTG | CCCTCTGAGA | CTGATGGCTA | CGTTGCCCCC | 3540 |
| CTGACCTGCA | GCCCCCAGCC | TGAATATGTG | AACCAGCCAG | ATGTTCGGCC | CCAGCCCCCT | 3600 |
| TCGCCCCGAG | AGGGCCCTCT | GCCTGCTGCC | CGACCTGCTG | GTGCCACTCT | GGAAAGGGCC | 3660 |
| AAGACTCTCT | CCCCAGGGAA | GAATGGGGTC | GTCAAAGACG | TTTTGCCTT | TGGGGGTGCC | 3720 |

-continued

| | | | | | | |
|---|---|---|---|---|---|---|
| GTGGAGAACC | CCGAGTACTT | GACACCCCAG | GGAGGAGCTG | CCCCTCAGCC | CCACCCTCCT | 3780 |
| CCTGCCTTCA | GCCCAGCCTT | CGACAACCTC | TATTACTGGG | ACCAGGACCC | ACCAGAGCGG | 3840 |
| GGGGCTCCAC | CCAGCACCTT | CAAAGGGACA | CCTACGGCAG | AGAACCCAGA | GTACCTGGGT | 3900 |
| CTGGACGTGC | CAGTGTGAAC | CAGAAGGCCA | AGTCCGCAGA | AGCCCTGATG | TGTCCTCAGG | 3960 |
| GAGCAGGGAA | GGCCTGACTT | CTGCTGGCAT | CAAGAGGTGG | GAGGGCCCTC | CGACCACTTC | 4020 |
| CAGGGGAACC | TGCCATGCCA | GGAACCTGTC | CTAAGGAACC | TTCCTTCCTG | CTTGAGTTCC | 4080 |
| CAGATGGCTG | GAAGGGGTCC | AGCCTCGTTG | GAAGAGGAAC | AGCACTGGGG | AGTCTTTGTG | 4140 |
| GATTCTGAGG | CCCTGCCCAA | TGAGACTCTA | GGGTCCAGTG | GATGCCACAG | CCCAGCTTGG | 4200 |
| CCCTTTCCTT | CCAGATCCTG | GGTACTGAAA | GCCTAGGGA | AGCTGGCCTG | AGAGGGGAAG | 4260 |
| CGGCCCTAAG | GGAGTGTCTA | AGAACAAAAG | CGACCCATTC | AGAGACTGTC | CCTGAAACCT | 4320 |
| AGTACTGCCC | CCCATGAGGA | AGGAACAGCA | ATGGTGTCAG | TATCCAGGCT | TTGTACAGAG | 4380 |
| TGCTTTTCTG | TTTAGTTTTT | ACTTTTTTTG | TTTTGTTTTT | TTAAAGACGA | AATAAAGACC | 4440 |
| CAGGGGAGAA | TGGGTGTTGT | ATGGGGAGGC | AAGTGTGGGG | GGTCCTTCTC | CACACCCACT | 4500 |
| TTGTCCATTT | GCAAATATAT | TTTGGAAAAC | | | | 4530 |

( 2 ) INFORMATION FOR SEQ ID NO:10:

( i ) SEQUENCE CHARACTERISTICS:
        ( A ) LENGTH: 757 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

| | | | | | | |
|---|---|---|---|---|---|---|
| CCCGGGGGTC | CTGGAAGCCA | CAAGGTAAAC | ACAACACATC | CCCCTCCTTG | ACTATGCAAT | 60 |
| TTTACTAGAG | GATGTGGTGG | GAAAACCATT | ATTTGATATT | AAAACAAATA | GGCTTGGGAT | 120 |
| GGAGTAGGAT | GCAAGCTCCC | CAGGAAAGTT | TAAGATAAAA | CCTGAGACTT | AAAAGGGTGT | 180 |
| TAAGAGTGGC | AGCCTAGGGA | ATTTATCCCG | GACTCCGGGG | GAGGGGGCAG | AGTCACCAGC | 240 |
| CTCTGCATTT | AGGGATTCTC | CGAGGAAAAG | TGTGAGAACG | GCTGCAGGCA | ACCCAGGCGT | 300 |
| CCCGGCGCTA | GGAGGGACGA | CCCAGGCCTG | CGCGAAGAGA | GGGAGAAAGT | GAAGCTGGGA | 360 |
| GTTGCCGACT | CCCAGACTTC | GTTGGAATGC | AGTTGGAGGG | GGCGAGCTGG | GAGCGCGCTT | 420 |
| GCTCCCAATC | ACAGGAGAAG | GAGGAGGTGG | AGGAGGAGGG | CTGCTTGAGG | AAGTATAAGA | 480 |
| ATGAAGTTGT | GAAGCTGAGA | TTCCCCTCCA | TTGGGACCGG | AGAAACCAGG | GGAGCCCCC | 540 |
| GGGCAGCCGC | GCGCCCCTTC | CCACGGGGCC | CTTTACTGCG | CCGCGCGCCC | GGCCCCCACC | 600 |
| CCTCGCAGCA | CCCCGCGCCC | CGCGCCCTCC | CAGCCGGGTC | CAGCCGGAGC | CATGGGGCCG | 660 |
| GAGCCGCAGT | GAGCACCATG | GAGCTGGCGG | CCTTGTGCCG | CTGGGGGCTC | CTCCTCGCCC | 720 |
| TCTTGCCCCC | CGGAGCCGCG | AGCACCCAAG | GTGGGTC | | | 757 |

( 2 ) INFORMATION FOR SEQ ID NO:11:

( i ) SEQUENCE CHARACTERISTICS:
        ( A ) LENGTH: 539 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

| | | | | | | |
|---|---|---|---|---|---|---|
| CCCGGGGGTC | CTGGAAGCCA | CAAGGTAAAC | ACAACACATC | CCCCTCCTTG | ACTATCAATT | 60 |
| TTACTAGAGG | ATGTGGTGGG | AAAACCATTA | TTTGATATTA | AAACAAATAG | GCTTGGGATG | 120 |

| GAGTAGGATG | CAAGCTCCCA | GGAAAGTTTA | AGATAAAACC | TGAGACTTAA | AAGGGTGTTA | 180 |
| --- | --- | --- | --- | --- | --- | --- |
| AGAGTGGCAG | CCTAGGGAAT | TTATCCCGGA | CTCCGGGGGA | GGGGCAGAG | TCACCAGCCT | 240 |
| CTGCATTTAG | GGATTCTCCG | AGGAAAGTG | TGAGAACGGC | TGCAGGCAAC | CCAGCTTCCC | 300 |
| GGCGCTAGGA | GGGACGCACC | CAGGCCTGCG | CGAAGAGAGG | GAGAAAGTGA | AGCTGGGAGT | 360 |
| TGCCACTCCC | AGACTTGTTG | GAATGCAGTT | GGAGGGGCG | AGCTGGGAGC | GCGCTTGCTC | 420 |
| CCAATCACAG | GAGAAGGAGG | AGGTGGAGGA | GGAGGGCTGC | TTGAGGAAGT | ATAAGAATGA | 480 |
| AGTTGTGAAG | CTGAGATTCC | CCTCCATTGG | GACCGGAGAA | ACCAGGGAGC | CCCCCCGGG | 539 |

(2) INFORMATION FOR SEQ ID NO:12:

(i) SEQUENCE CHARACTERISTICS:
        (A) LENGTH: 1717 base pairs
        (B) TYPE: nucleic acid
        (C) STRANDEDNESS: single
        (D) TOPOLOGY: linear (xi) SEQUENCE DESCRIPTION: SEQ ID NO:12:

| GAATTCGGCA | CGAGTACAGA | AGGTAAAGGC | TGTCTCTATG | GAGCCACTGG | CCATCCTGGT | 60 |
| --- | --- | --- | --- | --- | --- | --- |
| GCTGCTGTGC | TTTCCGATCT | GCTCAGCATA | TCCTCTGCAT | GGGGCAGTGA | GACAAGACCA | 120 |
| CTCAACCATG | GATCTTGCTC | AGCAATACCT | AGAAAATAC | TACAACTTTA | GAAAAAATGA | 180 |
| GAAACAATTT | TTCAAAAGAA | AGGACAGTAG | TCCTGTTGTC | AAAAAAATTG | AAGAAATGCA | 240 |
| GAAGTTCCTT | GGGCTGGAGA | TGACAGGGAA | GCTGGACTCG | AACACTGTGG | AGATGATGCA | 300 |
| CAAGCCCCGG | TGTGGTGTTC | CCGACGTTGG | TGGCTTCAGT | ACCTTTCCAG | GTTCACCCAA | 360 |
| ATGGAGGAAA | AACCACATCT | CCTACAGGAT | TGTGAATTAT | ACACTGGATT | TACCAAGAGA | 420 |
| GAGTGTGGAT | TCTGCCATTG | AGAGAGCTTT | GAAGGTCTGG | GAGGAGGTGA | CCCCACTCAC | 480 |
| ATTCTCCAGG | ATCTCTGAAG | GAGAGGCTGA | CATAATGATC | TCCTTTGCAG | TTGGAGAACA | 540 |
| TGGAGACTTT | TACCCTTTTG | ATGGAGTGGG | ACAGAGCTTG | GCTCATGCCT | ACCCACCTGG | 600 |
| CCCTGGATTT | TATGGAGATG | CTCACTTCGA | TGATGATGAG | AAATGGTCAC | TGGGACCCTC | 660 |
| AGGGACCAAT | TTATTCCTGG | TTGCTGCGCA | TGAACTTGGT | CACTCCCTGG | GTCTCTTTCA | 720 |
| CTCAAACAAC | AAAGAATCTC | TGATGTACCC | AGTCTACAGG | TTCTCCACGA | GCCAAGCCAA | 780 |
| CATTCGCCTT | TCTCAGGATG | ATATAGAGGG | CATTCAATCC | CTGTATGGAG | CCCGCCCCTC | 840 |
| CTCTGATGCC | ACAGTGGTTC | CTGTGCCCTC | TGTCTCTCCA | AAACCTGAGA | CCCCAGTCAA | 900 |
| ATGTGATCCT | GCTTTGTCCT | TGATGCAGT | CACCATGCTG | AGAGGGGAAT | TCCTATTCTT | 960 |
| TAAAGACAGG | CACTTCTGGC | GTAGAACCCA | GTGGAATCCC | GAGCCTGAAT | TCCATTTGAT | 1020 |
| TTCAGCATTT | TGGCCCTCTC | TTCCTTCAGG | CTTAGATGCT | GCCTATGAGG | CAAATAACAA | 1080 |
| GGACAGAGTT | CTGATTTTTA | AAGGAAGTCA | GTTCTGGGCA | GTCCGAGGAA | ATGAAGTCCA | 1140 |
| AGCAGGTTAC | CCAAAGAGGA | TCCACACTCT | TGGCTTTCCT | CCCACCGTGA | AGAAGATTGA | 1200 |
| TGCAGCTGTT | TTTGAAAAGG | AGAAGAAGAA | GACGTATTTC | TTTGTAGGTG | ACAAATACTG | 1260 |
| GAGATTTGAT | GAGACAAGAC | AGCTTATGGA | TAAAGGCTTC | CCGAGACTGA | TAACAGATGA | 1320 |
| CTTCCCAGGA | ATTGAGCCAC | AAGTTGATGC | TGTGTTACAT | GCATTTGGGT | TTTTTTATTT | 1380 |
| CTTCTGTGGA | TCATCACAGT | TCGAGTTTGA | CCCCAATGCC | AGGACGGTGA | CACACACACT | 1440 |
| GAAGAGCAAC | AGCTGGCTGT | TGTGCTGATT | ATCATGATGA | CAAGACATAT | ACAACACTGT | 1500 |
| AAAATAGTAT | TTCTCGCCTA | ATTTATTATG | TGTCATAATG | ATGAATTGTT | CCTGCATGTG | 1560 |
| CTGTGGCTCG | AGATGAGCCC | AGCAGATAGA | TGTCTTTCTT | AATGAACCAC | AGAGCATCAC | 1620 |
| CTGAGCACAG | AAGTGAAAGC | TTCTCGGTAC | ACTAGGTGAG | AGGATGCATC | CCCATGGGTA | 1680 |

5,518,885

41

-continued

42

CTTTATTGTT TAATAAAGAA CTTTATTTTT GAACCAT        1717

( 2 ) INFORMATION FOR SEQ ID NO:13:

( i ) SEQUENCE CHARACTERISTICS:
        ( A ) LENGTH: 650 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

| | | | | | | |
|---|---|---|---|---|---|---|
| GATATCAAGA | GGGTGATGCA | AACGTCCCAG | GAGTGTTCAA | GATAAAACCG | GAGACTGCAA | 60 |
| AGACGGGTAA | AGGGATGCTG | TGCTTTTAGG | AAGTGGATGA | GAACTGCAAG | CAAGCAAGCA | 120 |
| AGCAAGCAAG | CAAGCAAGCA | AGCAAGCAAG | CAAGCAAGCT | AGGCGTCGGG | GCACAGGGCA | 180 |
| GGCGCACCCA | GGCCTGCGCC | GGGAGGGAGA | AAGTGAAAGC | TGGGAGCAGC | CACTCCCAGT | 240 |
| CTTGCTGGAA | TGCAGTTGGA | GGGGTGGGGG | GGCGAGCCGA | GAGCGCGCGG | CTGCCAATCA | 300 |
| CGGGCGGAGG | AGGAGGTGGA | GGAGGAGGGC | TGCTCGAGGA | AGTGCGGCGT | GAAGTTGTGG | 360 |
| AGCTGAGATT | GCCCGCCGCT | GGGGACCCGG | AGCCCAGGAG | CGCCCCTTCC | CAGGCGGCCC | 420 |
| CTTCCGGCGC | CGGCCTGTGC | CTGCCCTCGC | CGCGCCCCCC | GCGCCCGCAG | CCTGGTCCAG | 480 |
| CCTGAGCCAT | GGGGCCGGAG | CCGCAATGAT | CATCATGGAG | CTGGCGGCCT | GGTGCCGCTG | 540 |
| GGGGTTCCTC | CTCGCCCTCC | TGCCCCCCGG | AATCGCGGGC | ACCCAAGGTG | GGTCTTGGCT | 600 |
| TGGGAAGGGC | TCTGGCCGCT | GTGCTGCCCA | CGGGCCGGAG | CGCGGAGCTC | | 650 |

( 2 ) INFORMATION FOR SEQ ID NO:14:

( i ) SEQUENCE CHARACTERISTICS:
        ( A ) LENGTH: 3955 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

| | | | | | | |
|---|---|---|---|---|---|---|
| CCGGGCCGGA | GCCGCAATGA | TCATCATGGA | GCTGGCGGCC | TGGTGCCGCT | GGGGGTTCCT | 60 |
| CCTCGCCCTC | CTGCCCCCCG | GAATCGCGGG | CACCCAAGTG | TGTACCGGCA | CAGACATGAA | 120 |
| GTTGCGGCTC | CCTGCCAGTC | CTGAGACCCA | CCTGGACATG | CTCCGCCACC | TGTACCAGGG | 180 |
| CTGTCAGGTA | GTGCAGGGCA | ACTTGGAGCT | TACCTACGTG | CCTGCCAATG | CCAGCCTCTC | 240 |
| ATTCCTGCAG | GACATCCAGG | AAGTTCAGGG | TTACATGCTC | ATCGCTCACA | ACCAGGTGAA | 300 |
| GCGCGTCCCA | CTGCAAAGGC | TGCGCATCGT | GAGAGGGACC | CAGCTCTTTG | AGGACAAGTA | 360 |
| TGCCCTGGCT | GTGCTAGACA | ACCGAGATCC | TCAGGACAAT | GTCGCCGCCT | CCACCCCAGG | 420 |
| CAGAACCCCA | GAGGGGCTGC | GGGAGCTGCA | GCTTCGAAGT | CTCACAGAGA | TCCTGAAGGG | 480 |
| AGGAGTTTTG | ATCCGTGGGA | ACCCTCAGCT | CTGCTACCAG | GACATGGTTT | TGTGGAAGGA | 540 |
| CGTCTTCCGC | AAGAATAACC | AACTGGCTCC | TGTCGATATA | GACACCAATC | GTTCCCGGGC | 600 |
| CTGTCCACCT | TGTGCCCCCG | CCTGCAAAGA | CAATCACTGT | TGGGGTGAGA | GTCCGGAAGA | 660 |
| CTGTCAGATC | TTGACTGGCA | CCATCTGTAC | CAGTGGTTGT | GCCCGGTGCA | AGGGCCGGCT | 720 |
| GCCCACTGAC | TGCTGCCATG | AGCAGTGTGC | CGCAGGCTGC | ACGGGCCCCA | AGCATTCTGA | 780 |
| CTGCCTGGCC | TGCCTCCACT | TCAATCATAG | TGGTATCTGT | GAGCTGCACT | GCCCAGCCCT | 840 |
| CGTCACCTAC | AACACAGACA | CCTTTGAGTC | CATGCACAAC | CCTGAGGGTC | GCTACACCTT | 900 |
| TGGTGCCAGC | TGCGTGACCA | CCTGCCCCTA | CAACTACCTG | TCTACGGAAG | TGGGATCCTG | 960 |
| CACTCTGGTG | TGTCCCCCGA | ATAACCAAGA | GGTCACAGCT | GAGGACGGAA | CACAGCGTTG | 1020 |

```
TGAGAAATGC AGCAAGCCCT GTGCTCGAGT GTGCTATGGT CTGGGCATGG AGCACCTTCG    1080
AGGGGCGAGG GCCATCACCA GTGACAATGT CCAGGAGTTT GATGGCTGCA AGAAGATCTT    1140
TGGGAGCCTG GCATTTTTGC CGGAGAGCTT TGATGGGGAC CCCTCCTCCG GCATTGCTCC    1200
GCTGAGGCCT GAGCAGCTCC AAGTGTTCGA AACCCTGGAG GAGATCACAG GTTACCTGTA    1260
CATCTCAGCA TGGCCAGACA GTCTCCGTGA CCTCAGTGTC TTCCAGAACC TTCGAATCAT    1320
TCGGGGACGG ATTCTCCACG ATGGCGCGTA CTCATTGACA CTGCAAGGCC TGGGGATCCA    1380
CTCGCTGGGG CTGCGCTCAC TGCGGGAGCT GGGCAGTGGA TTGGCTCTGA TTCACCGCAA    1440
CGCCCATCTC TGCTTTGTAC ACACTGTACC TTGGGACCAG CTCTTCCGGA ACCCACATCA    1500
GGCCCTGCTC CACAGTGGGA ACCGGCCGGA AGAGGACTTG TGCGTCTCGA GCGGCTTGGT    1560
CTGTAACTCA CTGTGTGCCC ACGGGCACTG CTGGGGGCCA GGGCCCACCC AGTGTGTCAA    1620
CTGCAGTCAT TTCCTTCGGG GCCAGGAGTG TGTGGAGGAG TGCCGAGTAT GGAAGGGGCT    1680
CCCCCGGGAG TATGTGAGTG ACAAGCGCTG TCTGCCGTGT CACCCCGAGT GTCAGCCTCA    1740
AAACAGCTCA GAGACCTGCT TTGGATCGGA GGCTGATCAG TGTGCAGCCT GCGCCCACTA    1800
CAAGGACTCG TCCTCCTGTG TGGCTCGCTG CCCCAGTGGT GTGAAACCGG ACCTCTCCTA    1860
CATGCCCATC TGGAAGTACC CGGATGAGGA GGGCATATGC CAGCCGTGCC CCATCAACTG    1920
CACCCACTCC TGTGTGGATC TGGATGAACG AGGCTGCCCA GCAGAGCAGA GAGCCAGCCC    1980
GGTGACATTC ATCATTGCAA CTGTAGAGGG CGTCCTGCTG TTCCTGATCT TAGTGGTGGT    2040
CGTTGGAATC CTAATCAAAC GAAGGAGACA GAAGATCCGG AAGTATACGA TGCGTAGGCT    2100
GCTGCAGGAA ACTGAGTTAG TGGAGCCGCT GACGCCCAGC GGAGCAATGC CAACCAGGC    2160
TCAGATGCGG ATCCTAAAAG AGACGGAGCT AAGGAAGGTG AAGGTGCTTG GATCAGGAGC    2220
TTTTGGCACT GTCTACAAGG GCATCTGGAT CCCAGATGGG GAGAATGTGA AAATCCCCGT    2280
GGCTATCAAG GTGTTGAGAG AAAACACATC TCCTAAAGCC AACAAAGAAA TTCTAGATGA    2340
AGCGTATGTG ATGGCTGGTG TGGGTTCTCC GTATGTGTCC CGCCTCCTGG GCATCTGCCT    2400
GACATCCACA GTACAGCTGG TGACACAGCT TATGCCCTAC GGCTGCCTTC TGGACCATGT    2460
CCGAGAACAC CGAGGTCGCC TAGGCTCCCA GGACCTGCTC AACTGGTGTG TTCAGATTGC    2520
CAAGGGGATG AGCTACCTGG AGGACGTGCG GCTTGTACAC AGGGACCTGG CTGCCCGGAA    2580
TGTGCTAGTC AAGAGTCCCA ACCACGTCAA GATTACAGAT TTCGGGCTGG CTCGGCTGCT    2640
GGACATTGAT GAGACAGAGT ACCATGCAGA TGGGGGCAAG GTGCCCATCA AATGGATGGC    2700
ATTGGAATCT ATTCTCAGAC GCCGGTTCAC CCATCAGAGT GATGTGTGGA GCTATGGAGT    2760
GACTGTGTGG GAGCTGATGA CTTTTGGGGC CAAACCTTAC GATGGAATCC CAGCCCGGGA    2820
GATCCCTGAT TTGCTGGAGA AGGGAGAACG CCTACCTCAG CCTCCAATCT GCACCATTGA    2880
TGTCTACATG ATTATGGTCA AATGTTGGAT GATTGACTCT GAATGTCGCC CGAGATTCCG    2940
GGAGTTGGTG TCAGAATTTT CACGTATGGC GAGGGACCCC AGCGTTTTG TGGTCATCCA    3000
GAACGAGGAC TTGGGCCCAT CCAGCCCCAT GGACAGTACC TTCTACCGTT CACTGCTGGA    3060
AGATGATGAC ATGGGTGACC TGGTAGACGC TGAAGAGTAT CTGGTGCCCC AGCAGGGATT    3120
CTTCTCCCCG GACCCTACCC CAGGCACTGG GAGCACAGCC CATAGAAGGC ACCGCAGCTC    3180
GTCCACCAGG AGTGGAGGTG GTGAGCTGAC ACTGGGCCTG GAGCCCTCGG AAGAAGGGCC    3240
CCCCAGATCT CCACTGGCTC CCTCGGAAGG GGCTGGCTCC GATGTGTTTG ATGGTGACCT    3300
GGCAATGGGG GTAACCAAAG GGCTGCAGAG CCTCTCTCCA CATGACCTCA GCCCTCTACA    3360
GCGGTACAGC GAGGACCCCA CATTACCTCT GCCCCCCGAG ACTGATGGCT ATGTTGCTCC    3420
```

| | | | | | |
|---|---|---|---|---|---|
| CCTGGCCTGC | AGCCCCCAGC | CCGAGTATGT | GAACCAATCA | GAGGTTCAGC | CTCAGCCTCC | 3480
| TTTAACCCCA | GAGGGTCCTC | TGCCTCCTGT | CCGGCCTGCT | GGTGCTACTC | TAGAAAGACC | 3540
| CAAGACTCTC | TCTCCTGGGA | AGAATGGGGT | TGTCAAAGAC | GTTTTTGCCT | TCGGGGGTGC | 3600
| TGTGGAGAAC | CCTGAATACT | TAGTACCGAG | AGAAGGCACT | GCCTCTCCGC | CCCACCCTTC | 3660
| TCCTGCCTTC | AGCCCAGCCT | TTGACAACCT | CTATTACTGG | GACCAGAACT | CATCGGAGCA | 3720
| GGGGCCTCCA | CCAAGTAACT | TTGAAGGGAC | CCCCACTGCA | GAGAACCTG | AGTACCTAGG | 3780
| CCTGGATGTA | CCTGTATGAG | ACGTGTGCAG | ACGTCCTGTG | CTTTCAGAGT | GGGGAAGGCC | 3840
| TGACTTGTGG | TCTCCATCGC | CACAAAGCAG | GGAGAGGGTC | CTCTGGCCAC | ATTACATCCA | 3900
| GGGCAGACGG | CTCTACCAGG | AACCTGCCCC | GAGGAACCTT | TCCTTGCTGC | TTGAA | 3955

( 2 ) INFORMATION FOR SEQ ID NO:15:

( i ) SEQUENCE CHARACTERISTICS:
        ( A ) LENGTH: 721 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

| | | | | | |
|---|---|---|---|---|---|
| GATATCCCAG | AGAGTCTTGG | AAGTCACCAG | TTAGACATAA | CACATTCCCT | TCCCAGGCTG | 60
| ATTTTACCTG | AGGATGTGGC | GACAAACCCA | TTATCTGGTA | TTAAGAGTGT | GATGCAAACG | 120
| TTCCAAGAGT | ATCCAAGATA | AAACCCACCC | AAGACTGCAA | AGAGGGGTAA | AGAGATGCCC | 180
| TGCTTTTAGG | AAGTGGGTGA | GAACTGCAAG | CAAGCAAGCA | AGCGAGGCGT | CAGGGCACAG | 240
| CGCGACGCAC | CCAGCCTGCG | CCGGGAGGGA | GAAAGTGAAG | CTGGGAGCAG | CCACTCCCAG | 300
| TCTTGCTGGA | AGTCAGTTGG | AGGGGTGGGG | GGGCGAGCCG | GGAGCGCGCG | GCTCCCAATC | 360
| ACGGGCGGCG | GAGGAGGCGG | AGGAGGAGGG | CTGCTCGAGG | AAGTGCGGCG | TGAAGTTGTG | 420
| GAGCTGAGAT | TGCCCGCCGC | TGGGGACCCG | GAGCCCAGGA | GCGCCCCTTC | CCAGGCGGCC | 480
| CCTTCCGGCG | CCGCGCCTGT | GCCTGCCCTC | GCCGCGCCCC | GGCCCGCAGC | CTGGTCCAGC | 540
| CTGAGCCATG | GGGCCGGAGC | CGCAGTGATC | ATCATGGAGC | TGGCGGCCTG | GTGCCGTTGG | 600
| GGGTTCCTCC | TCGCCCTCCT | GTCCCCCGGA | GCCGCGGGTA | CCCAAGGTGG | GTCTTGGCTT | 660
| GGGGAGGGCT | CGGGCCGCTA | CGCTGCCCAC | GGCGGCCGGA | GCCGCGGGGC | CCCGAGAGCT | 720
| C | | | | | | 721

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

Y S S C C M N S S S         10

( 2 ) INFORMATION FOR SEQ ID NO:17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
GGTGGGGGGG                                                                                      10
```

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

```
GTGGGGGGGG                                                                                      10
```

( 2 ) INFORMATION FOR SEQ ID NO:19:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
GAATGAAGTT GTGAAGCTGA GATTCCCCTC C                                                              31
```